United States Patent
Li

(10) Patent No.: US 11,207,387 B2
(45) Date of Patent: *Dec. 28, 2021

(54) METHOD AND DRUG FOR PREVENTING AND TREATING OBESITY

(71) Applicant: Talengen International Limited, Wanchai (HK)

(72) Inventor: Jinan Li, Guangdong (CN)

(73) Assignee: TALENGEN INTERNATIONAL LIMITED, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/470,173

(22) PCT Filed: Dec. 15, 2017

(86) PCT No.: PCT/CN2017/116562
§ 371 (c)(1),
(2) Date: Jun. 14, 2019

(87) PCT Pub. No.: WO2018/108161
PCT Pub. Date: Jun. 21, 2018

(65) Prior Publication Data
US 2019/0328849 A1 Oct. 31, 2019

(30) Foreign Application Priority Data
Dec. 15, 2016 (WO) ................ PCT/CN2016/110172

(51) Int. Cl.
*A61K 38/48* (2006.01)
*A61P 3/04* (2006.01)
*A61P 9/10* (2006.01)

(52) U.S. Cl.
CPC .............. *A61K 38/484* (2013.01); *A61P 3/04* (2018.01); *A61P 9/10* (2018.01)

(58) Field of Classification Search
CPC ............. A61K 38/484; A61P 9/10; A61P 3/04
See application file for complete search history.

(56) References Cited

U.S. PATENT DOCUMENTS

| | | | |
|---|---|---|---|
| 4,245,051 A | 1/1981 | Reich | |
| 4,774,338 A | 9/1988 | Priesnitz | |
| 4,996,050 A | 2/1991 | Tsukada | |
| 5,597,800 A | 1/1997 | Eibl et al. | |
| 5,637,299 A | 6/1997 | Mcdonagh | |
| 5,776,452 A | 7/1998 | Eibl | |
| 7,056,943 B2 | 6/2006 | Elokdah | |
| 7,067,492 B2 | 6/2006 | Ny et al. | |
| 8,357,147 B2 | 1/2013 | Burkinshaw | |
| 10,729,750 B2 | 8/2020 | Ny | |
| 10,864,257 B2 | 12/2020 | Li | |
| 2002/0103129 A1 | 8/2002 | Ge | |
| 2002/0159992 A1 | 10/2002 | Henkin | |
| 2003/0026798 A1 | 2/2003 | Zimmerman | |
| 2003/0054988 A1 | 3/2003 | Ji | |
| 2003/0147876 A1 | 8/2003 | Ni | |
| 2004/0038891 A1 | 2/2004 | Bisgaier | |
| 2004/0043026 A1 | 3/2004 | Tuan | |
| 2004/0247564 A1 | 12/2004 | Itescu | |
| 2005/0124036 A1 | 6/2005 | Susilo | |
| 2008/0017694 A1 | 1/2008 | Schnell et al. | |
| 2008/0200387 A1* | 8/2008 | Wu ........................... | A61P 7/00 514/13.3 |
| 2009/0093442 A1 | 4/2009 | Lynch | |
| 2009/0123582 A1 | 5/2009 | Kuwahara | |
| 2009/0208448 A1 | 8/2009 | Solomon | |
| 2009/0239868 A1 | 9/2009 | Muto | |
| 2009/0275513 A1 | 11/2009 | Rebbeor | |
| 2010/0099600 A1 | 4/2010 | Ny | |
| 2010/0184661 A1 | 7/2010 | Luo | |
| 2011/0039766 A1 | 2/2011 | Szeto | |
| 2011/0318812 A1 | 12/2011 | Hunt | |
| 2012/0058537 A1 | 3/2012 | Mahboudi | |
| 2012/0114630 A1 | 5/2012 | Zwaal | |
| 2014/0121241 A1 | 5/2014 | Nakajima | |
| 2014/0273275 A1 | 9/2014 | Jacobs | |
| 2015/0224073 A1 | 8/2015 | Green | |
| 2016/0200831 A1 | 7/2016 | Pritsker | |
| 2018/0369345 A1 | 12/2018 | Li | |
| 2019/0015485 A1 | 1/2019 | Li | |

(Continued)

FOREIGN PATENT DOCUMENTS

CA 2145841 A1 10/1995
CA 2475277 A1 8/2003
(Continued)

OTHER PUBLICATIONS

Lipek et al., "Obesogenic environments: environmental approaches to obesity prevention", J Pediatr Endocrinol Metab. May 2015; 28(5-6): 485-95. doi: 10.1515/jpem-2015-0127 (Year: 2015).*
U.S. Appl. Nos. 16/469,611; 16/469,618; 16/470,174; 16/624,170, filed 2016.*
Alessi, M. C. et al. (Aug. 24, 2006). "PAI-1 and the Metabolic Syndrome: Links, Causes, and Consequences," Arterioscler Thromb Vasc Biol. 26(10):2200-2207.
Beier, J.I. et al. (Jan. 31, 2012). "Alcoholic Liver Disease and the Potential Role of Plasminogen Activator Inhibitor-1 and Fibrin Metabolism," Exp. Biol. Med. 237(1):1-9, 19 pages.

(Continued)

Primary Examiner — Ruth A Davis
(74) Attorney, Agent, or Firm — Morrison & Foerster LLP

(57) ABSTRACT

The present invention relates to a method for preventing and/or treating overweight/obesity and their related conditions, comprising administering an effective amount of plasminogen to a subject susceptible to or suffering from obesity and its related conditions, to reduce an abnormal/excessive fat deposition at various sites of the body. The present invention further relates to a medicament for preventing and/or treating obesity, and its use in the preparation of a medicament.

16 Claims, 7 Drawing Sheets

Specification includes a Sequence Listing.

(56) References Cited

U.S. PATENT DOCUMENTS

| | | |
|---|---|---|
| 2019/0083586 A1 | 3/2019 | Li |
| 2019/0231854 A1 | 8/2019 | Robitaille |
| 2019/0328850 A1 | 10/2019 | Li |
| 2019/0351033 A1 | 11/2019 | Li |
| 2020/0085920 A1 | 3/2020 | Li |
| 2020/0206324 A1 | 7/2020 | Li |

FOREIGN PATENT DOCUMENTS

| | | |
|---|---|---|
| CA | 2770688 A1 | 2/2011 |
| CA | 2707266 A1 | 12/2013 |
| CA | 3002915 A1 | 5/2017 |
| CA | 3008185 A1 | 6/2017 |
| CN | 1451746 A | 10/2000 |
| CN | 1408431 A | 4/2003 |
| CN | 1662548 A | 8/2005 |
| CN | 1668312 A | 9/2005 |
| CN | 1668645 | 9/2005 |
| CN | 1720051 A | 1/2006 |
| CN | 1726191 A | 1/2006 |
| CN | 1768138 A | 5/2006 |
| CN | 101015686 A | 8/2007 |
| CN | 101132788 A | 2/2008 |
| CN | 101563100 A | 10/2009 |
| CN | 101573134 A | 11/2009 |
| CN | 101628113 A | 1/2010 |
| CN | 101686994 A | 3/2010 |
| CN | 101842093 A | 9/2010 |
| CN | 101897925 A | 12/2010 |
| CN | 101918548 A | 12/2010 |
| CN | 102121023 A | 7/2011 |
| CN | 102123721 A | 7/2011 |
| CN | 102154253 A | 8/2011 |
| CN | 102188699 A | 9/2011 |
| CN | 102199587 A | 9/2011 |
| CN | 102378753 A | 3/2012 |
| CN | 102482338 A | 5/2012 |
| CN | 102532326 A | 7/2012 |
| CN | 102647994 A | 8/2012 |
| CN | 102660564 A | 9/2012 |
| CN | 103384722 A | 11/2013 |
| CN | 103656630 A | 3/2014 |
| CN | 103703140 A | 4/2014 |
| CN | 103764163 A | 4/2014 |
| CN | 104274449 A | 1/2015 |
| CN | 105008323 A | 10/2015 |
| CN | 105705520 A | 6/2016 |
| CN | 1856319 A | 11/2016 |
| EP | 0307847 A2 | 3/1989 |
| EP | 0192667 B1 | 10/1994 |
| EP | 0631786 A1 | 1/1995 |
| EP | 0674906 A2 | 10/1995 |
| EP | 1666469 A1 | 6/2006 |
| EP | 0200145 A2 | 12/2008 |
| EP | 2201946 A1 | 6/2010 |
| EP | 3391902 A1 | 10/2018 |
| EP | 3556391 A1 | 10/2019 |
| JP | 62153224 A | 7/1987 |
| JP | 2005525798 A | 9/2005 |
| JP | 2010502600 A | 1/2010 |
| JP | 2010515694 A | 5/2010 |
| JP | 2019500423 A | 1/2019 |
| JP | 2019500424 A | 1/2019 |
| TW | 201722468 | 7/2017 |
| TW | I624268 B | 5/2018 |
| TW | 201822791 A | 7/2018 |
| TW | 201822792 A | 7/2018 |
| TW | 201822799 | 7/2018 |
| TW | 201822805 A | 7/2018 |
| TW | 201822806 A | 7/2018 |
| TW | 201822809 A | 7/2018 |
| TW | 201822810 A | 7/2018 |
| TW | 201829448 A | 8/2018 |
| TW | 200908973 A | 3/2019 |
| WO | 199512407 A1 | 5/1995 |
| WO | 199900420 A1 | 1/1999 |
| WO | WO200048595 A1 | 8/2000 |
| WO | WO200049871 A1 | 8/2000 |
| WO | 200240510 A2 | 5/2002 |
| WO | 2003014145 A2 | 2/2003 |
| WO | 2003033019 A2 | 4/2003 |
| WO | 200240510 A3 | 6/2003 |
| WO | 2003033019 A3 | 7/2003 |
| WO | 2003066842 A2 | 8/2003 |
| WO | 2003014145 A3 | 12/2003 |
| WO | 2003066842 A3 | 6/2004 |
| WO | 2006095713 A1 | 9/2006 |
| WO | 2006102395 A2 | 9/2006 |
| WO | 2006122249 A2 | 11/2006 |
| WO | 2006102395 A3 | 5/2007 |
| WO | 2006122249 A3 | 6/2007 |
| WO | WO2008026999 A2 | 3/2008 |
| WO | WO2008027000 A2 | 3/2008 |
| WO | 2008083615 A1 | 7/2008 |
| WO | WO2009089059 A2 | 7/2009 |
| WO | WO2010076655 A1 | 7/2010 |
| WO | WO2010083570 A1 | 7/2010 |
| WO | 2010125148 A2 | 11/2010 |
| WO | 2010125148 A3 | 1/2011 |
| WO | WO2011004011 A1 | 1/2011 |
| WO | 2011139973 A2 | 11/2011 |
| WO | 2011139973 A3 | 3/2012 |
| WO | WO2012135729 A2 | 10/2012 |
| WO | WO2013024074 A1 | 2/2013 |
| WO | WO2014070983 A1 | 5/2014 |
| WO | 2015023752 A1 | 2/2015 |
| WO | 2015026494 A2 | 2/2015 |
| WO | 2015026494 A3 | 11/2015 |
| WO | 2017077380 A1 | 5/2017 |
| WO | WO2017101869 A1 | 6/2017 |
| WO | WO2018107684 A1 | 6/2018 |
| WO | WO2018107685 A1 | 6/2018 |
| WO | WO2018107688 A1 | 6/2018 |
| WO | WO2018107692 A1 | 6/2018 |
| WO | WO2018107707 A1 | 6/2018 |
| WO | WO2018108161 A1 | 6/2018 |
| WO | 2018234861 A1 | 12/2018 |

OTHER PUBLICATIONS

Brouwers, M.C.G.J. et al. (2008, e-pub. Feb. 8, 2008). "Plasma PAI-1 Levels Are Independently Related to Fatty Liver and Hypertriglyceridemia in Familial Combined Hyperlipidemia, Involvement of Apolipoprotein E," Thrombosis Research 122:466-472.

Chang, M.L. et al. (Dec. 31, 2015). "Plasminogen Activator Inhibitor-1 Is Independently Associated With Non-Alcoholic Fatty Liver Disease Whereas Leptin and Adipo-Nectin Vary Between Genders," Journal of Gastroenterology and Hepatology, 30:329-336.

Chen, W. et al. (Sep. 30, 2009). "Effects of Fibrate on the Pathophysiology of Kidney," International Journal of Endocnnology and Metabolism 29(5):332-334. English Abstract.

Crandall, D. L. et al. (October 20006, e-pub. Jul. 6, 2006). "Modulation of Adipose Tissue Development by Pharmacological Inhibition of PAI-1," Arterioscler Thromb Vasc Biol. 26(10): 2209-2215.

Darvall, K. A. L. et al. (Dec. 20, 2006). "Obesity and Thrombosis," European Journal of Vascular and Endovascular Surgery 33(2):223-233.

Deng, Y. et al. (Jan. 31, 2005). "Relationship Between Phlegmstasis Syndrome and Fibrinolytic Status in Patients with Non-alcoholic Fatty Liver," Chinese Journal of Integrated Traditional and Western Medicine pp. 22-24. English Abstract.

Forsgren, M. et al. (Mar. 19, 1999). "Plasminogen [*Homo sapiens*]," NCBI Reference Sequence: NP_000292, 4 pages.

International Search Report, dated Aug. 16, 2017, PCT Application No. PCT/CN2017/089047, 5 pages.

International Search Report, dated Aug. 25, 2017, PCT Application No. PCT/CN2017/089046, 6 pages.

International Search Report, dated Mar. 19, 2018, PCT Application No. PCT/CN2017/116562, 4 pages.

International Search Report, dated Sep. 13, 2017, PCT Application No. PCT/CN2017/089052, 6 pages.

(56) References Cited

OTHER PUBLICATIONS

International Search Report, dated Sep. 15, 2017, PCT Application No. PCT/CN2017/089051, 6 pages.
International Search Report, dated Sep. 20, 2017, PCT Application No. PCT/CN2017/089048, 5 pages.
International Search Report, dated Sep. 6, 2017, PCT Application No. PCT/CN2017/089049, 6 pages.
Joshi-Barve, S. et al. (Jul. 31, 2015). "Alcoholic, Nonalcoholic, and Toxicant-Associated Steatohepatitis: Mechanistic Similarities and Differences," CMGH 1:356-367.
Kaji, H. (Oct. 31, 2016). "Adipose Tissue-Derived Plasminogen Activator Inhibitor-1 Function and Regulation," Comprehensive Physiology 6:1873-1896.
Kurt, B. et al. (Mar. 3, 2015). "Lipoprotein(a): Clinical Aspects and Future Challenges," Clin. Res. Cardiol. 10 (Suppl.):26-32.
Lijnen, H. R. et al. (2007, e-pub. Aug. 23, 2007). "Angiogenesis and Obesity," Cardiovascular Research 78(2):286-293.
Liu, J.Y. (2014, e-pub. Oct. 28, 2014). "Ethanol and Liver: Recent Insights Into the Mechanisms of Ethanol-Induced Fatty Liver," World J. Gastroenterol, 20(40):14672-14685.
Ma, L.-J. et al. (Feb. 2004). "Prevention of Obesity and Insulin Resistance in Mice Lacking Plasminogen Activator Inhibitor 1," Diabetes 53:336-346.
Rupnick, M.A. et al. (Aug. 6, 2002). "Adipose Tissue Mass Can Be Regulated Through the Vasculature," PNAS 99(16):10730-10735.
Miles, L.A. et al. (Nov. 11, 2016). "Abstract 19088 the Plasminogen Receptor, Plg-Rkt, Regulates Metabolic Homeostasis and Promotes Healthy Adipose Function," Circulation 134(Suppl 1), 2 pages.
Plow, E. F. et al. (Jul. 31, 2014)., "The Functions of Plasminogen in Cardiovascular Disease," Trends in Cardiovascular Medicine 14(5):180-186.
Restrepo, L. et al. (2009, e-pub. Aug. 22, 2009). "Impact of Hyperlipidemia and Statins on Ischemic Stroke Outcomes after Intra-Arterial Fibrinolysis and Percutaneous Mechanical Embolectomy," Cerebrovasc Dis. 28:384-390.
Shen, H. et al. (Apr. 28, 2009). "Roles of Adipocytokines in the Pathogenesis of Non-alcoholic Fatty Liver Disease " World Chinese Journal of Digestology 17(12):1212-1217. English Abstract.
Skurk, T. et al. (2004, e-pub. Aug. 28, 2004). "Obesity and Impaired Fibrinolysis: Role of Adipose Production of Plasminogen Activator Inhibitor-1," International Journal of Obesity 28:1357-1364.
Thuy, S. et al. (Dec. 31, 2008). "Nonalcoholic Fatty Liver Disease in Humans Is Associated with Increased Plasma Endotoxin and Plasminogen Activator Inhibitor 1 Concentrations and with Fructose Intake," The Journal of Nutrition 138:1452-1455.
Written Opinion for the International Searching Authority, dated Aug. 16, 2017, PCT Application No. PCT/CN2017/089047, 6 pages.
Written Opinion for the International Searching Authority, dated Aug. 25, 2017, PCT Application No. PCT/CN2017/089046, 5 pages.
Written Opinion for the International Searching Authority, dated Sep. 13, 2017, PCT Application No. PCT/CN2017/089052, 5 pages.
Written Opinion for the International Searching Authority, dated Mar. 19, 2018, PCT Application No. PCT/CN2017/116562, 6 pages.
Written Opinion for the International Searching Authority, dated Sep. 15, 2017, PCT Application No. PCT/CN2017/089051, 5 pages.
Written Opinion for the International Searching Authority, dated Sep. 20, 2017, PCT Application No. PCT/CN2017/089048, 5 pages.
Written Opinion for the International Searching Authority, dated Sep. 6, 2017, PCT Application No. PCT/CN2017/089049, 4 pages.
Wu, M. et al. (Sep. 23, 2016). "The Research Progress of Relationship Between Lipid Regulation and Diabetic Nephropathy," Medicine and Philosophy 557(9B):66-69. English Abstract.
Zhang, Y. et al. (Apr. 30, 2005). "Fibrinolytic Activity and Type 2 Diabetes Mellitus and Macroangiopathy Thereof," Foreign Medical Sciences 25:42-44. English Abstract.
Jiang, G. et al. (Dec. 31, 1991). "Research Progress of Antithrombotic and Thrombolytic Drugs," Chinese Journal of Biochemical and Pharmaceutics. 1:1-4. English Abstract.

Ma, D. et al. (Aug. 10, 1994). "Molecular Relations Between Thrombosis and Atherosclerosis," Cerebrovascular Diseases Foreign Medical Sciences 2(4):195-197. English Abstract.
Mehta, J. L. et al. (Mar. 1, 1995). "Recombinant Lys-Plasminogen, but Not Glu-Plasminogen, Improves Recombinant Tissue-Type Plasminogen Activator-Induced Coronary Thrombolysis in Dogs," Journal of the American College of Cardiology 25(3):753-760.
Wu, M. et al. (May 15, 2007). "Research of Relationship Between Postprandial Hyperlipidemia, Carotid Atherosclerosis and Fibrinolytic Activity in Patients With Type 2 Diabetes Mellitus," Journal of Shandong University Health Science 45(5):503-506. English Abstract.
Xiao, Q. et al. (Sep. 1997). "Plasminogen Deficiency Accelerates Vessel Wall Disease in Mice Predisposed to Atherosclerosis" Proceedings of the National Academy of Sciences 94:10335-10340.
Yang, S. et al. (Mar. 30, 2002). "Coronary Angiographic Analysis of Coronary Heart Disease Complicated With Type 2 Diabetes," Practical Journal of Medicine & Pharmacy 19(3):164 and 165. English Equivalent Abstract Only.
Ye, P. et al. (Dec. 31, 1998). "The Association of Hypertriglyceridemia with Plasma Haemostatic and Fibrinolytic Activities," Chinese Journal of Arteriosc Lerosis. 6(4):333-335. English Abstract.
Yin, G. et al. (Feb. 28, 2005). "Expression and Purification of the Gene Clone of Human Plasminogen Kringle5 Region," Academic Journal of Shanghai Second Medical University 25(02):151-154. English Abstract.
International Search Report, dated Sep. 14, 2017, PCT Application No. PCT/CN2017/089043, 7 pages.
Written Opinion of the International Searching Authority dated Sep. 14, 2017, PCT Application No. PCT/CN2017/089043, 5 pages.
International Search Report, dated Sep. 8, 2017, PCT Application No. PCT/CN2017/089044, 7 pages.
Written Opinion of the International Searching Authority dated Sep. 8, 2017, PCT Application No. PCT/CN2017/089044, 5 pages.
International Search Report, dated Sep. 8, 2017, PCT Application No. PCT/CN2017/089045, 7 pages.
Written Opinion of the International Searching Authority dated Sep. 8, 2017, PCT Application No. PCT/CN2017/089045, 5 pages.
U.S. Appl. No. 16/469,611, Jinan, L. filed Jun. 13, 2019. (pursuant to the waiver of 37 C.F.R. § 1.98(a)(2)(iii) issued by the Office on Sep. 21, 2004).
U.S. Appl. No. 16/469,599, Jinan, L. filed Jun. 13, 2019. (pursuant to the waiver of 37 C.F.R. § 1.98(a)(2)(iii) issued by the Office on Sep. 21, 2004).
U.S. Appl. No. 16/470,160, Jinan, L. filed Jun. 14, 2019. (pursuant to the waiver of 37 C.F.R. § 1.98(a)(2)(iii) issued by the Office on Sep. 21, 2004).
U.S. Appl. No. 16/469,168, Jinan, L. filed Jun. 13, 2019. (pursuant to the waiver of 37 C.F.R. § 1.98(a)(2)(iii) issued by the Office on Sep. 21, 2004).
U.S. Appl. No. 16/470,174, Jinan, L. filed Jun. 14, 2019. (pursuant to the waiver of 37 C.F.R. § 1.98(a)(2)(iii) issued by the Office on Sep. 21, 2004).
Aisina, R.B. et al. (2014). "Structure and Function of Plasminogen/Plasmin System," Russian Journal of Bioorganic Chemistry 40(6):590-604.
Anderie, K. et al. (1988). "Review of Studies with Plasminogen Concentrates and Proposals for Further Therapeutic Strategies with Plasminogen Concentrates," Haemostasis 18(Suppl.1):165-175.
Badylak, S.F. (1991). "Enhancement of the Thrombolytic Efficacy of Prourokinase by Lys-Plasminogen in a Dog Model of Artbrial Thrombosis," Thrombosis Research 62:115-126.
Basic Medicine (Dec. 31, 1998). Encyclopedia of Chinese Medicine Shanghai Science and Technology Publishing House. 907:2-3. English Abstract.
Bezerra, J.A. (1999). "Plasminogen Deficiency Leads to Impaired Remodeling After a Toxic Injury to the Liver," PNAS 96(26):15143-15148.
Bookstein, J.J. MD et al. (2000). "Plasminogen-Enriched Pulse-Spray Thrombolysis With tPA: Further Developments," Journal of Vascular and Interventional Radiology 11(10):1353-1362.
Butera, D. et al. (Mar. 15, 2015). "NP-000292.1—Plasminogen Isoform 1 Precursor," GenBank 4 pages.

(56) References Cited

OTHER PUBLICATIONS

Chang, P.C. et al. (Jan. 1, 2010). "Human Plasminogen Kringle 1-5 Reduces Atherosclerosis and Neointima Formation in Mice by Suppressing the Inflammatory Signaling Pathway," Journal of Thrombosis and Haemostasis 8(1):194-201.
Danese, C. et al. (Nov. 30, 1996). "Lipoproteina(a)e Plasminogeno Nella Malattia Aterosclerotia," Minerva Cardioangiologica 44(11):529-533. Abstract Only.
Das, R. et al. (Mar. 19, 2013), "Macrophage Gene Expression and Foam Cellformation Are Regulated by Plasminogen," Circulation 127(11):1209-1218.
Feuerstein, G.Z. et al. (1995). "Cardioprotection and Thrombolysis by Anistrephase in Anesthetized Dogs," Journal of Cardiovascular Pharmacology 25:625-633.
Getz, G.S. et al. (2010). "HDL Apolipoprotein-Related Peptides in the Treatment of Atherosclerosis and Other Inflammatory Disorders," Curr. Pharm. Des. 16(28):3173-3184, 21 pages.
Gong, W. (May 31, 2014). "Clinical Diabetes, Section IV Pathophysiology of Type 2 Diabetes Three Factors, Octet and High Glucose and Lipid Toxicity," ages 6-8. English Abstract.
Hoover-Plow, J. et al. (Dec. 31, 2002). "In Vivo Plasminogen Deficiency Reduces Fat Accumulation," Thromb Haemost. 87:1011-1019.
Huang, C. (Dec. 31, 2003). "Recombinant Tissue Plasminogen Activator Protects Experimental Ischemic Myocardium," Journal of Practical Medicine 19(9):953-954. English Abstract.
Kopec, A.K. et al. (Jun. 2016, e-pub. May 4, 2016). "Role of Fibrin(ogen) in Progression of Liver Disease: Guilt by Association?" Semin Thromb Hemost. 42(4):397-407, 18 pages.
Kostka, T. et al. (2009, e-pub. Mar. 28, 2008)."Cardiovascular Disease (CVD) Risk Factors, Physical Activity (PA) and Plasma Plasminogen (Pig) in a Random Sample of Community-Dwelling Elderly," Archives of Gerontology and Geriatrics 48(3):300-305.
Kunadian, V. et al. (Apr. 1, 2012). "Thrombolytic and Myocardial Infarction," Cardiovascular Therapeutics 30(2):e81-e88.
Landskroner, K. et al. (Dec. 31, 2005). "Cross-Species Pharmacologic Evaluation of Plasmin as a Direct-Acting Thrombolytic Agent: Ex Vivo Evaluation for Large Animal Model Development," J Vasc Interv Radiol. 16:369-377.
Li, L.-V. et al. (Mar. 1, 2005). "Angiopoietins and Tie2 in Health and Disease," Pediatric Enoocrinology Reviews 2(3):399-408.
Li, Z. et al. (Apr. 30, 2007). "Research Progress of Liver Fibrosis Treatment," Journal of Liaoning Medical College 28(2):46-48.
Liu, M.Y. et al. (Oct. 31, 2010). "Plasminogen: Structure, Function and Evolution," Journal of Ocean University of China 40(10):69-74. English Abstract.
Lv, W,-S. (Apr. 30, 1990). "The Treatment of Obesity," Guangdong Science and Technology Press p. 123. English Abstract.
Mao, D.D.B.L (Apr. 26, 2011). "Study on the Pathogenesis of Diabetic Cardiomyopathy," Baidu Wenku. English Abstract.
Mayo Clinic (1998). "Heart Failure 1998-2020," 4 pages.
Mitchell, J.W. et al. (Jun. 1, 2006). "Plasminogen Inhibits TNF α-Induced Apoptosis in Monocytes," Blood 107(11):4383-4390.
Morishita, R. et al. (1988). "Novel Therapeutic Atrategy for Atherosclerosis: Ribozyme Oligonucleotides Against Apolipoprotein(a) Selectively Inhibit Apolipoprotein(a) but Not Plasminogen Gene Expression," Circulation 98:1898-1904.
Naito, G. (1986). "The Formulation and Clinical Experience of Plasminogen Activator System," Journal of Japan Society of Blood Transfusion 32(6):590-593. English Abstract.
Nanada, I. (1981). "Effect of Urokinase on Heart and Brain Infarctions Combined With Diabetic Patients," Clinical and Research 58(2):659-665. English Abstract.
Nannan, Z. et al. (Jul. 31, 2014). "Biochemical Testing Technology, Chapter 6 Determination of Glucose in Body Fluid," p. 75. English Abstract.
Neubauer et al. (Apr. 1995). "Accumulation and Cellular Localization of Fibrinogen/Fibrin During Short-Term and Long-Term Rat Liver Injury," Gastroenterology 108(4):1124-1135.
Okada, K. et al. (Sep. 2008). "Binding of Plasminogen to Hepatocytes Isolated From Injured Mice Liver and Nonparenchymal Cell-Dependent Proliferation of Hepatocytes," Blood Coagulation and Fibrinolysis 19:503-511.
Peng, Y. et al. (Dec. 31, 2005). "Protective Effects of Recombinant Tissue Plasminogen Activator on Acute Myocardial Infarction in Senile Rats," Chinese Journal of Gerontology 25(12):1517-1518. English Abstract.
Pohl, J.F. et al. (Dec. 2001). "Plasminogen Deficiency Leads to Impaired Lobular Reorganization and Matrix Accumulation after Chronic Liver Injury," American Journal of Pathology 159(6):2179-2186.
Schmitz, V. et al. (2007). "Plasminogen Fragment K1-5 Improves Survival in a Murine Hepatocellular Carcinoma Model," Gut 56:271-278.
Schuster, V. et al. (Dec. 31, 2007). "Plasminogen Deficiency," Journal of Thrombosis and Haemostasis 5:2315-2322.
Science Daily (2008). "How Diabetes Drives Atherosclerosis" 2 pages.
Sha, J. et al. (Mar. 22, 2002). "Plasminogen Reduces Atherosclerosis in Apo(a) Transgenic Mice," Annual Meeting of Professional Research Scientists on Experimental Biology 16(5):A823.
Shanmukhappa, K. et al. (May 8, 2009), "Plasmin-Mediated Proteolysis Is Required for Hepatocyte Growth Factor Activation During Liver Repair," The Journal of Biological Chemistry 284(19):12917-12923.
Sima, J. et al. (Apr. 23, 2004. e-pub. Mar. 23, 2004). "The Effect of Angiostatin on Vascular Leakage and VEGF Expression in Rat Retina," FEBS Letters 564(1-2):19-23.
Sundell, B. et al. (Aug. 5, 1997). "Reduction in Stent and Vascular Graft Thrombosis and Enhancement of Thrombolysis by Recombinant Lys-Plasminogen in Nonhuman Primates," 96(3):941-948.
Tahara, M. et al. (1999). "Hepatocyte Growth Factor Leads to Recovery From Alcohol-Induced Fatty Liver in Rats," J Clin Invest. 103(3):313-320.
Takamura T. et al, (Mar. 26, 2004). "Genes for Systemic Vascular Complications Are Differentially Expressed in the Lives of Type 2 Diabetic Patients," Diabetologia 47:638-647.
Takeshi, A. (1981). "Progress of Thrombolytic Therapy and Its Clinical Effect," Blood and Vessel 12(4):493-501. English Abstract.
Tanaka, K. (2000). "PP-1250 Involvement of Tissue Line System in Liver Regenerating: Examination Using Plasminogen Gene Knock-out Mice," Journal of Japan Surgical Society 101:520, English Abstract, 3 pages.
Uniprot Protein Database Blast Results, Human Plasminogen Amino Acids 581-808 accessed on Aug. 23, 2020, 5 pages.
Vogten, J.M. et al. (2004, e-pub. Jan. 10, 2004). "Angiostatin Inhibits Experimental Liver Fibrosis in Mice," International Journal of Colorectal Disease 19(4):387-394.
Wang, E. (Sep. 30, 2003). Editor-in-Chief of Pathology, Higher Education Press p. 69. English Abstract.
Wang, G. (Aug. 31, 2007). "Effects of Actilyse on Hemorheology in Rats with Acute Ischemic Myocardial Injure," Chinese Journal of Cardiovascular Rehabilitation Medicine 16(4):369-371, English Abstract.
Wang, L. et al. (Nov. 30, 2004). "Protective Effects of rt-PA on Experimental Myocardial Ischemia in Rats," Journal of Cardiovascular and Pulmonary Diseases 23(4):238-239, English Abstract.
Wang, Z. (Feb. 28, 2007). "Clinical Treatment of Endocrine Diseases and Rational Use of Drug," Scientific and Technological Literature Press pp. 164-176. English Abstract .(Fat Metabolism Disorder).
Xu, B. et al. (Aug. 31, 2014). "Diagnosis and Nursing of Clinical Internal Diseases," Kunming, Yunnan Science and Technology Press p. 138. English Abstract.
Xu, D. et al. (Feb. 2012). "Therapeutic Effect of Recombinant Tissue Plasminogen Activator on Acute Cerebral Infarction," Prevention and Treatment of Cerebral-Vascular Disease 12(1):37-39. English Abstract.
Yang, L. et al. (2004). "Changes of Fbrinolytic Parameters in Coronary Heart Disease," Chinese Journal of Thrombosis and Hemostasis 10(1):8-10. English Abstract.

(56) References Cited

OTHER PUBLICATIONS

Yu, D. et al. (Jan. 31, 2009). "Measurements of Plasmin-Alpha2 Antiplasmin Complex in Patients with Liver Cirrohosis and Hepatocarcinoma," Laboratory Medicine and Clinic 6(2):92-93. English Abstract.

Zhang, S.X. et al. (Jan. 1, 2006). "Therapeutic Potential of Angiostatin in Diabetic Nephropathy," J. Am. Soc. Nephrol. 17:475-486, 12 pages.

Zhao, Y. et al. (Jul. 31, 2009). "Changes of Coagulation and Fibrinolysis System Function in Patients With Metabolic Syndrome," Journal of Difficult Diseases 8(7):397-399. English Abstract.

Bhatt, H.B. et al. (2015). "Fatty Liver Disease in Diabetes Mellitus," HepatoBiliary Surg. Nutr. 4(2): 101 -108.

European Office Action, dated Feb. 16, 2021, for European Patent Application No. 16874928.1, 9 pages.

Harvard Heart Letter (Sep. 2016). "Fatty Liver Disease and Your Heart: About One in Three Adults Has Nonalcoholic Fatty Liver Disease, An Often-Silent Condition Closely Linked to Heart Disease," Harvard Health Publishing, 3 pages.

Harvard Women's Health Watch (Feb. 2012). "What To Do About Nonalcoholic Fatty Liver Disease," Harvard Health Publishing, 4 pages.

Kawao, N. et al. (2010, e-pub. Jan. 10, 2010). "Role of Plasminogen in Macrophage Accumulation During Liver Repair," Thrombosis Research 125:e214-e221.

Liver Center (Jan. 20, 2021). "Nonalcoholic Fatty Liver Disease," UC San Diego Health, 4 pages.

Ogbru, O. et al. (Jan. 18, 2016). "Type 2 Oral Diabetes Mediations (Oral)," MedicineNet.com, 3 pages.

Shen, Y. et al. (Jun. 14, 2012). "Plasminogen is a Key Proinflammatory Regulator That Accelerates the Healing of Acute and Diabetics Wounds," Thrombosis and Hemostatis 119(24):5879-5887.

Xu, L. et al. (2012). "Diabetic Angiopathy and Angiogenic Defects." Fibrogenesis & Tissue Repair 5:1-9.

* cited by examiner

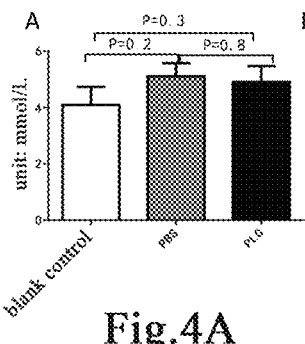 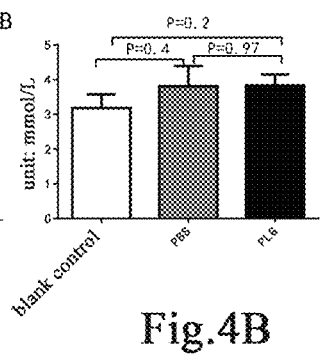 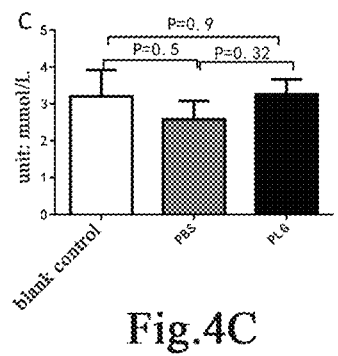
Fig.4A  Fig.4B  Fig.4C
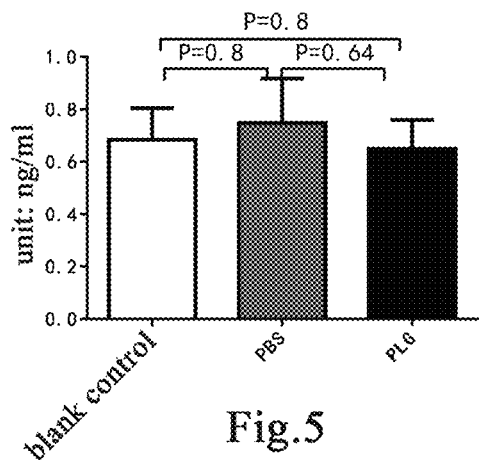
Fig.5
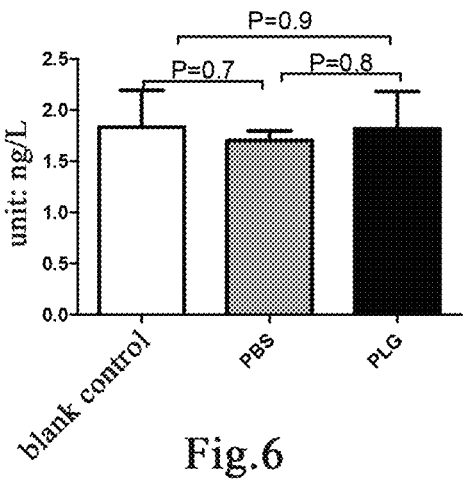
Fig.6

METHOD AND DRUG FOR PREVENTING AND TREATING OBESITY

CROSS REFERENCE TO RELATED APPLICATIONS

This application is a National Phase application under 35 U.S.C. § 371 of International Application No. PCT/CN2017/116562, filed Dec. 15, 2017, which claims priority to International Application No. PCT/CN2016/110172, filed Dec. 15, 2016, the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 794922000800SEQLIST.TXT, date recorded: Jun. 7, 2019, size: 46 KB).

TECHNICAL FIELD

The present invention relates to a method and a medicament for preventing and/or treating obesity and its related conditions.

BACKGROUND ART

Obesity refers to excessive accumulation and/or abnormal distribution of fat in the body. According to the definition of the World Health Organization (WHO), overweight and obesity refer to excessive and/or abnormal accumulation of fat in the body that may impair health. As early as 1948, WHO defined obesity as a disease and added it to the international classification of disease (ICD). In June 2013, for the first time in the history, the American Medical Association (AMA) officially declared obesity a disease requiring medical interventions for prevention and treatment [1]. Overweight and obesity are the risk factors for a variety of diseases, comprising cardiovascular and cerebrovascular diseases (heart disease, hypertension, dyslipidemia, and cerebral stroke), type 2 diabetes mellitus, musculoskeletal diseases (osteoarthritis, etc.), digestive system diseases (a gallbladder disease), sleep apnea or respiratory disorders, certain cancers (endometrial cancer, breast cancer, and colon cancer), etc. [2] According to the WHO data, in 2014, more than 1.9 billion adults worldwide were overweight, and more than 600 million of them were obese [2]. The overweight rate of adults in China is 31.5%, and the obesity rate is 12.2% [3]. Overweight and obesity have become important diseases affecting the health of residents.

Clinically, body fat is indirectly reflected by measuring the external characteristics of the body. Common measurement indexes are body mass index (BMI) and waist circumference (WC). BMI is the most important index for diagnosis of obesity, and waist circumference can reflect accumulation extent of abdominal fat. Currently, the classification criteria of the World Health Organization are overweight with BMI≥25 kg·m$^2$ and obesity with BMI≥30 kg·m$^2$. The ranking is substantially based on data from European Caucasians. When BMI is the same, Asians have a higher percentage of body fat than westerners, and abdominal obesity of Asians is more severe [4].

Based on the research on the relevant data of obesity in China, the Guidelines for the Prevention and Control of Overweight and Obesity in Chinese Adults (Trial) in 2003 states that the case of BMI≥24 kg·m$^2$ should belong to overweight in Chinese adults and the case of BMI≥28 kg·m$^2$ should belong to obesity; and the Expert Consensus on Prevention and Treatment of Obesity in Chinese Adults in 2011 states that male waist circumference ≥90 cm and female waist circumference ≥85 cm are considered as the determination criteria of abdominal obesity.

The treatment of obesity is mainly divided into lifestyle intervention, drug therapy and surgical treatment. At present, evidence-based medical evidence recommends lifestyle intervention as the first-line therapeutic regimen. The Guidelines for the Prevention and Control of Overweight and Obesity in Chinese Adults (Trial) states that drug therapy should be recommended when lifestyle intervention is ineffective, i.e., 5% weight loss cannot be achieved and BMI is still greater than 28. Drug therapy is also recommended for overweight patients with one complication (cardiovascular disease, hypertension, type 2 diabetes mellitus, etc.) who have failed to respond to life intervention.

The weight-loss drugs can be divided into: central appetite suppressants, appetite-suppressing gastrointestinal hormones, and drugs acting on the periphery to interfere with nutrient absorption and increase nutrient metabolism. Two of the three long-term weight-loss drugs that are central appetite suppressants have been discontinued: rimonabant and sibutramine were discontinued by the EMEA in October 2008 and January 2010, respectively, because they may increase the risk of mental and cardiovascular diseases [5-6]. The once widespread use left the weight-loss drug market in a vacancy after the suspension. In recent years, the role of gastrointestinal hormones in regulating appetite and controlling blood glucose has become a hot research topic. Some of these drugs have obvious effects of appetite suppression and weight loss in animal experiments; however, their safety and effective dose still need to be further studied in more clinical trials. The drugs acting on the periphery target at two aspects: 1. the gastrointestinal tract to reduce fat absorption, the drugs being lipase inhibitors and sodium-glucose co-transporter 2 (SGLT2) inhibitors; 2. adipose tissues to reduce fat synthesis and promote fat hydrolysis, the drugs mainly being enzymes on the lipid metabolic pathway. Lipase inhibitors reduce the absorption of fat in the diet by inhibiting lipase in the gastrointestinal tract and pancreas. Orlistat has been shown to be effective in weight loss with few side effects. However, severe hepatic injury was reported in 13 users in the United States, and the FDA recently decided to urge its manufacturers to update product specifications [7].

Drug efficacy and safety should be assessed at least monthly for the first 3 months of drug therapy, and should be assessed every 3 months thereafter [8]. The safety of weight-loss drugs is the main reason for their limited application, and the curative effect of the drugs on weight loss is also limited. Therefore, drug therapy is still an auxiliary means of obesity treatment, and lifestyle improvement with the help of medical professionals is a preferred method to treat overweight and obesity. Obesity is a chronic disease. There are no drugs that can produce lasting weight loss benefits. Only long-term medication can maintain weight. In the face of a growing number of overweight and obese patients, it is an urgent desire to find safer and more effective weight-loss drugs.

SUMMARY OF THE INVENTION

The present invention relates to the following items:

1. A method for preventing or treating obesity in a subject, comprising administering an effective amount of plasminogen to the subject.

2. The method of item 1, wherein the plasminogen treats obesity by reducing abnormal or excessive lipid deposition in and around a tissue and an organ and/or in an abdominal cavity.

3. The method of item 2, wherein the plasminogen reduces abnormal or excessive lipid deposition in a subcutis, in a heart, a liver, lungs, kidneys, blood vessels, a mesentery, a peritoneum, and a body cavity, and around an organ.

4. The method of item 1, wherein the plasminogen treats obesity by lowering a level of blood lipid, particularly triglyceride and low-density lipoprotein, in a subject.

5. The method of any one of items 1 to 4, wherein the obesity is simple obesity or obesity secondary to other diseases.

6. A method for preventing or treating obesity in a subject, comprising administering an effective amount of plasminogen to the subject, wherein the obesity is secondary to an endocrine disorder disease, a glucose metabolism disease, a liver disease, a kidney disease, a cardiovascular disease, an intestinal disease, a thyroid disease, a gallbladder or biliary tract disease, excessive drinking, and a drug effect.

7. A method for preventing and/or treating obesity complicated with a disease in a subject, comprising administering an effective amount of plasminogen to the subject, wherein the obesity complicated with a disease comprises obesity complicated with an endocrine disease, obesity complicated with a metabolic disease, obesity complicated with a cardiovascular disease, obesity complicated with a digestive system disease, and obesity complicated with a degenerative disease.

8. The method of item 7, wherein the obesity comprises obesity complicated with diabetes mellitus, obesity complicated with hypertension, obesity complicated with atherosclerosis, obesity complicated with a liver disease, and obesity complicated with osteoporosis.

9. A method for preventing or treating an obesity-induced complication, comprising administering an effective amount of plasminogen to a subject, wherein the obesity-induced complication comprises cardiovascular and cerebrovascular diseases, a metabolic disease, a musculoskeletal disease, a digestive system disease, sleep apnea, and a respiratory disorder.

10. The method of item 9, wherein the complication is hypertension, diabetes mellitus, coronary heart disease, angina pectoris, myocardial infarction, arrhythmia, atherosclerosis, cerebral thrombosis, cerebral hemorrhage, osteoarthritis, hyperosteogeny, cholecystitis, fatty liver, and hepatic cirrhosis.

11. A method for reducing the risk of atherosclerosis in a subject, comprising administering an effective amount of plasminogen to the subject.

12. The method of item 11, wherein the plasminogen reduces the risk of atherosclerosis in the subject by treating obesity.

13. A method for reducing the onset risk of obesity in a subject, comprising administering an effective amount of plasminogen to the subject to reduce abnormal or excessive fat deposition in and around a tissue and an organ, in a subcutis, or in an abdominal cavity.

16. Use of plasminogen in the manufacture of a medicament for preventing or treating obesity in a subject.

17. The use of item 16, wherein the plasminogen reduces abnormal or excessive fat deposition in a subject in one or more ways selected from:
  1) reducing abnormal or excessive lipid deposition in one or more sites selected from: a subcutis, a heart, a liver, lungs, kidneys, blood vessels, a mesentery, a peritoneum, and a body cavity, and around an organ,
  2) promoting clearance of hepatic fat, and
  3) promoting clearance of lipid in blood to reduce the onset risk of heart disease in the subject.

18. A method for lowering blood lipid in a subject, comprising administering an effective amount of plasminogen to the subject.

19. The method of item 18, wherein the plasminogen lowers a serum triglyceride level and a low-density lipoprotein level.

20. A method for reducing the onset risk of atherosclerosis or heart disease in a subject, comprising administering an effective amount of plasminogen to the subject to alleviate abnormal or excessive lipid deposition on a blood vessel wall.

21. A method for treating obesity in a subject, comprising administering an effective amount of plasminogen to the subject to promote clearance of deposited fat by the liver.

22. A method for treating obesity in a subject, comprising administering an effective amount of plasminogen to the subject, wherein the plasminogen reduces fat in the subject in one or more ways selected from:
  1) reducing abnormal or excessive lipid deposition in one or more sites selected from: a subcutis, a heart, a liver, lungs, kidneys, blood vessels, a mesentery, a peritoneum, and a body cavity, and around an organ,
  2) promoting clearance of hepatic fat, and
  3) promoting clearance of lipid in blood.

23. The method of item 22, wherein the obesity is simple obesity or obesity secondary to other diseases.

24. The method of item 23, wherein the obesity is secondary to an endocrine disorder disease, a glucose metabolism disease, a liver disease, a kidney disease, a cardiovascular disease, an intestinal disease, a thyroid disease, a gallbladder or biliary tract disease, excessive drinking, and a drug effect.

25. The method of any one of items 1 to 24, wherein the plasminogen is administered in combination with one or more other drugs or therapeutic means.

26. The method of item 25, wherein the one or more other drugs comprises a drug for treating hypertension, a drug for treating diabetes mellitus, a drug for treating atherosclerosis, a drug for treating chronic glomerulonephritis, a drug for treating chronic pyelonephritis, a drug for treating nephrotic syndrome, a drug for treating renal insufficiency, a drug for treating uremia, a drug for treating kidney transplantation, a drug for treating fatty liver, a drug for treating hepatic cirrhosis, and a drug for treating obesity.

27. The method of item 26, wherein the other drugs comprise: a hypolipidemic drug, an anti-platelet drug, an antihypertensive drug, a vasodilator, a hypoglycemic drug, an anticoagulant drug, a thrombolytic drug, a hepatoprotective drug, an anti-arrhythmia drug, a cardiotonic drug, a diuretic drug, an anti-infective drug, an antiviral drug, an immunomodulatory drug, an inflammatory regulatory drug, an anti-tumor drug, a hormone drug, and thyroxine.

28. The method of item 27, wherein the drugs comprise hypolipidemic drugs: statins; fibrates; niacin; cholestyramine; clofibrate; unsaturated fatty acids such as Yishouning, Xuezhiping, and Xinmaile; and alginic sodium diester; anti-platelet drugs: aspirin; dipyridamole; clopidogrel; and cilostazol; vasodilators: hydralazine; nitroglycerin, and isosorbide dinitrate; sodium nitroprusside; α1-receptor blockers such as prazosin; α-receptor blockers such as phentolamine; β2-receptor stimulants such as salbutamol; captopril, enalapril; nifedipine, diltiazem; and salbutamol, loniten, prostaglandin, and atrial natriuretic peptide; thrombolytic drugs: urokinase, and streptokinase; tissue-type plasminogen activators; single chain urokinase-type plasminogen activators; and a TNK tissue-type plasminogen activator; and anticoagulant drugs: heparin; enoxaparin; nadroparin; and bivalirudin.

29. The method of any one of items 1 to 28, wherein the plasminogen has at least 75%, 80%, 85%, 90%, 95%, 96%, 97%, 98% or 99% sequence identity with SEQ ID No. 2, 6, 8, 10 or 12, and still has the plasminogen activity.

30. The method of any one of items 1 to 29, wherein the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No. 2, 6, 8, 10 or 12, and still has the plasminogen activity.

31. The method of any one of items 1 to 30, wherein the plasminogen is a protein that comprises a plasminogen active fragment and still has the plasminogen activity. 32. The method of any one of items 1 to 31, wherein the plasminogen is selected from Glu-plasminogen, Lys-plasminogen, mini-plasminogen, micro-plasminogen, delta-plasminogen or their variants that retain the plasminogen activity.

33. The method of any one of items 1 to 32, wherein the plasminogen is a natural or synthetic human plasminogen, or a variant or fragment thereof that still retains the plasminogen activity.

34. The method of any one of items 1 to 33, wherein the plasminogen is an ortholog of human plasminogen from a primate or a rodent, or a variant or fragment thereof that still retains the plasminogen activity.

35. The method of any one of items 1 to 34, wherein the amino acids of the plasminogen are as shown in SEQ ID No. 2, 6, 8, 10 or 12.

36. The method of any one of items 1 to 35, wherein the plasminogen is a natural human plasminogen.

37. The method of any one of items 1 to 36, wherein the subject is a human.

38. The method of any one of items 1 to 37, wherein the subject has a lack or deficiency of plasminogen.

39. The method of item 38, wherein the lack or deficiency is congenital, secondary and/or local.

40. A plasminogen for use in the method of any one of items 1 to 39.

41. A pharmaceutical composition, comprising a pharmaceutically acceptable carrier and the plasminogen for use in the method of any one of items 1 to 39.

42. A preventive or therapeutic kit comprising: (i) the plasminogen for use in the method of any one of items 1 to 39, and (ii) a means for delivering the plasminogen to the subject.

43. The kit of item 42, wherein the means is a syringe or a vial.

44. The kit of item 42 or 43, further comprising a label or an instruction for use indicating the administration of the plasminogen to the subject to implement the method of any one of items 1 to 39.

45. An article of manufacture, comprising:
a container comprising a label; and
(i) the plasminogen for use in the method of any one of items 1 to 39 or a pharmaceutical composition comprising the plasminogen, wherein the label indicates the administration of the plasminogen or the composition to the subject to implement the method of any one of items 1 to 39.

46. The kit of any one of items 42 to 44 or the article of manufacture of item 45, further comprising one or more additional means or containers containing other drugs.

47. The kit or the article of manufacture of item 46, wherein the other drugs are selected from a group of: a hypolipidemic drug, an anti-platelet drug, an antihypertensive drug, a vasodilator, a hypoglycemic drug, an anticoagulant drug, a thrombolytic drug, a hepatoprotective drug, an anti-arrhythmia drug, a cardiotonic drug, a diuretic drug, an anti-infective drug, an antiviral drug, an immunomodulatory drug, an inflammatory regulatory drug, an anti-tumor drug, a hormone drug, and thyroxine.

48. A weight-loss drug comprising plasminogen.

49. A weight-loss product comprising plasminogen.

50. Use of plasminogen for weight loss.

The present invention further relates to the use of plasminogen in the preparation of a medicament, a pharmaceutical composition, an article of manufacture, and a kit for use in the above-mentioned method.

In one aspect, the present invention relates to a method for preventing and/or treating obesity and its related conditions in a subject, comprising administering a prophylactically and/or therapeutically effective amount of plasminogen to the subject. The present invention further relates to the use of plasminogen for preventing and/or treating obesity and its related conditions in a subject. The present invention further relates to the use of plasminogen in the preparation of a medicament, a pharmaceutical composition, an article of manufacture, and a kit for preventing and/or treating obesity and its related conditions in a subject. Furthermore, the present invention further relates to a plasminogen for preventing and/or treating obesity and its related conditions in a subject. The present invention further relates to a medicament, a pharmaceutical composition, an article of manufacture, and a kit comprising plasminogen which are useful for preventing and/or treating obesity and its related conditions in a subject.

In some embodiments, the obesity is obesity caused by excessive diet. In some embodiments, the obesity is secondary obesity, for example secondary to a fat metabolism disorder disease, e.g., a fat metabolism disorder elicited or accompanied by an endocrine disorder disease, a glucose metabolism disease, a liver disease, a kidney disease, a cardiovascular disease, an intestinal disease, a thyroid disease, a gallbladder or biliary tract disease, drinking, and a drug therapy. In some embodiments, the fat metabolism disorder is a fat metabolism disorder elicited or accompanied by hypertension, diabetes mellitus, chronic hepatitis, hepatic cirrhosis, renal injury, chronic glomerulonephritis, chronic pyelonephritis, nephrotic syndrome, renal insufficiency, kidney transplantation, uremia, hypothyroidism, obstructive cholecystitis, obstructive cholangitis, and a drug or hormone therapy. In some embodiments, the fat metabolism disorder is hyperlipemia, hyperlipoproteinemia, fatty liver, atherosclerosis, obesity, and a visceral fat deposition.

In yet another aspect, the present invention relates to a method for preventing and/or reducing an abnormal or excessive fat deposition in a body tissue and an organ of a subject, comprising administering an effective amount of plasminogen to the subject. The present invention further relates to the use of plasminogen for preventing and/or reducing an abnormal or excessive fat deposition in a body tissue and an organ of a subject. The present invention further relates to the use of plasminogen in the preparation of a medicament, a pharmaceutical composition, an article of manufacture, and a kit for preventing and/or reducing an abnormal or excessive fat deposition in a body tissue and an organ of a subject. Furthermore, the present invention also relates to a plasminogen for preventing and/or reducing an abnormal or excessive fat deposition in a body tissue and an organ of a subject. The present invention further relates to a medicament, a pharmaceutical composition, an article of manufacture, and a kit comprising plasminogen which are useful for preventing and/or reducing an abnormal or excessive fat deposition in a body tissue and an organ of a subject.

In yet another aspect, the present invention relates to a method for preventing and/or treating a condition caused by an abnormal or excessive fat deposition in a body tissue and an organ of a subject, comprising administering an effective amount of plasminogen to the subject. The present invention further relates to the use of plasminogen for preventing and/or treating a condition caused by an abnormal or excessive fat deposition in a body tissue and an organ of a subject. The present invention further relates to the use of plasminogen in the preparation of a medicament, a pharmaceutical composition, an article of manufacture, and a kit for preventing and/or treating a condition caused by an abnormal or excessive fat deposition in a body tissue and an organ of a subject. Furthermore, the present invention also relates to a medicament, a pharmaceutical composition, an article of manufacture, and a kit comprising plasminogen which are useful for preventing and/or treating a condition caused by an abnormal or excessive fat deposition in a body tissue and an organ of a subject.

In some embodiments, the abnormal or excessive fat deposition in a body tissue and an organ refers to an abnormal or excessive fat deposition in blood, a subcutaneous tissue, a vascular wall and an internal organ. In some embodiments, the condition resulting from the abnormal or excessive fat deposition in a body tissue and an organ comprises obesity, hyperlipemia, hyperlipoproteinemia, fatty liver, atherosclerosis, a lipid-induced cardiac damage, a lipid-induced renal damage, and a lipid-induced islet damage.

In yet another aspect, the present invention relates to a method for preventing and/or treating obesity resulting from a fat metabolism disorder in a subject, comprising administering an effective amount of plasminogen to the subject. The present invention further relates to the use of plasminogen for preventing and/or treating obesity resulting from a fat metabolism disorder in a subject. The present invention further relates to the use of plasminogen in the preparation of a medicament, a pharmaceutical composition, an article of manufacture, and a kit for preventing and/or treating obesity resulting from a fat metabolism disorder in a subject. Furthermore, the present invention also relates to a plasminogen for preventing and/or treating obesity resulting from a fat metabolism disorder in a subject. The present invention further relates to a medicament, a pharmaceutical composition, an article of manufacture, and a kit comprising plasminogen which are useful for preventing and/or treating obesity resulting from a fat metabolism disorder in a subject. In some embodiments, the condition comprises obesity, hyperlipemia, hyperlipoproteinemia, fatty liver, atherosclerosis, a lipid-induced heart tissue injury, and a lipid-induced renal injury.

In yet another aspect, the present invention relates to a method for treating a disease in a subject by reducing an abnormal or excessive fat deposition, comprising administering an effective amount of plasminogen to the subject. The present invention further relates to the use of plasminogen for treating a disease in a subject by reducing an abnormal or excessive fat deposition. The present invention further relates to the use of plasminogen in the preparation of a medicament, a pharmaceutical composition, an article of manufacture, and a kit for treating a disease in a subject by reducing an abnormal or excessive fat deposition. Furthermore, the present invention also relates to a plasminogen for treating a disease in a subject by reducing an abnormal or excessive fat deposition. The present invention further relates to a medicament, a pharmaceutical composition, an article of manufacture, and a kit comprising plasminogen which are useful for treating a disease in a subject by reducing an abnormal or excessive fat deposition.

In some embodiments, the disease comprises atherosclerosis, coronary heart disease, angina pectoris, myocardial infarction, arrhythmia, fatty liver, hepatic cirrhosis, cerebral ischemia, cerebral infarction, renal insufficiency, nephrotic syndrome, renal insufficiency, and obesity.

In yet another aspect, the present invention relates to a method for preventing and/or treating a lipid-induced injury in a tissue and an organ of a subject, comprising administering an effective amount of plasminogen to the subject. The present invention further relates to the use of plasminogen for preventing and/or treating a lipid-induced injury in a tissue and an organ of a subject. The present invention further relates to the use of plasminogen in the preparation of a medicament, a pharmaceutical composition, an article of manufacture, and a kit for preventing and/or treating a lipid-induced injury in a tissue and an organ of a subject. Furthermore, the present invention also relates to a plasminogen for preventing and/or treating a lipid-induced injury in a tissue and an organ of a subject. The present invention further relates to a medicament, a pharmaceutical composition, an article of manufacture, and a kit comprising plasminogen which are useful for preventing and/or treating a lipid-induced injury in a tissue and an organ of a subject.

In some embodiments, the tissue and the organ comprise an arterial wall, a heart, a liver, a kidney, and a pancreas.

In yet another aspect, the present invention relates to a method for improving hyperlipemia in a subject, comprising administering an effective amount of plasminogen to the subject. The present invention further relates to the use of plasminogen for improving hyperlipemia in a subject. The present invention further relates to the use of plasminogen in the preparation of a medicament, a pharmaceutical composition, an article of manufacture, and a kit for improving hyperlipemia in a subject. Furthermore, the present invention also relates to a plasminogen for improving hyperlipemia in a subject. The present invention further relates to a medicament, a pharmaceutical composition, an article of manufacture, and a kit comprising plasminogen which are useful for improving hyperlipemia in a subject.

In some embodiments, the hyperlipemia is selected from one or more of: hypercholesterolemia, hypertriglyceridemia, combined hyperlipemia, and hypo-high-density lipoproteinemia.

In yet another aspect, the present invention relates to a method for reducing the risk of atherosclerosis in a subject, comprising administering an effective amount of plasminogen to the subject. The present invention further relates to the use of plasminogen for reducing the risk of atherosclerosis in a subject. The present invention further relates to the use of plasminogen in the preparation of a medicament, a pharmaceutical composition, an article of manufacture, and a kit for reducing the risk of atherosclerosis in a subject. Furthermore, the present invention also relates to a plasminogen for reducing the risk of atherosclerosis in a subject.

The present invention further relates to a medicament, a pharmaceutical composition, an article of manufacture, and a kit comprising plasminogen which are useful for reducing the risk of atherosclerosis in a subject.

In some embodiments, the subject suffers from hypertension, obesity, diabetes mellitus, chronic hepatitis, hepatic cirrhosis, renal injury, chronic glomerulonephritis, chronic pyelonephritis, nephrotic syndrome, renal insufficiency, kidney transplantation, uremia, hypothyroidism, obstructive cholecystitis, or obstructive cholangitis, or the subject takes a drug or hormone that affects fat metabolism. In some embodiments, the plasminogen reduces the risk of atherosclerosis in a subject in one or more ways selected from: lowering a total cholesterol level, a triglyceride level, and a low-density lipoprotein level in blood, and elevating a high-density lipoprotein level in blood.

In yet another aspect, the present invention relates to a method for treating a disease in a subject by improving hyperlipemia, comprising administering an effective amount of plasminogen to the subject. The present invention further relates to the use of plasminogen for treating a disease by improving hyperlipemia in a subject. The present invention further relates to the use of plasminogen in the preparation of a medicament, a pharmaceutical composition, an article of manufacture, and a kit for treating a disease by improving hyperlipemia in a subject. Furthermore, the present invention also relates to a plasminogen for treating a disease by improving hyperlipemia in a subject. The present invention further relates to a medicament, a pharmaceutical composition, an article of manufacture, and a kit comprising plasminogen which are useful for treating a disease by improving hyperlipemia in a subject.

In some embodiments, the condition comprises diabetes mellitus, hypertension, atherosclerosis, coronary heart disease, angina pectoris, myocardial infarction, arrhythmia, chronic hepatitis, fatty liver, hepatic cirrhosis, cerebral circulation insufficiency, cerebral ischemia, cerebral infarction, chronic nephritis, chronic pyelonephritis, renal insufficiency, nephrotic syndrome, uremia, and obesity.

In yet another aspect, the present invention relates to a method for preventing and/or treating a hyperlipemia-related condition in a subject, comprising administering an effective amount of plasminogen to the subject. The present invention further relates to the use of plasminogen for preventing and/or treating a hyperlipemia-related condition in a subject. The present invention further relates to the use of plasminogen in the preparation of a medicament, a pharmaceutical composition, an article of manufacture, and a kit for preventing and/or treating a hyperlipemia-related condition in a subject. Furthermore, the present invention also relates to a plasminogen for preventing and/or treating a hyperlipemia-related condition in a subject. The present invention further relates to a medicament, a pharmaceutical composition, an article of manufacture, and a kit comprising plasminogen which are useful for preventing and/or treating a hyperlipemia-related condition in a subject. In some embodiments, the condition comprises diabetes mellitus, hypertension, atherosclerosis, coronary heart disease, angina pectoris, myocardial infarction, arrhythmia, chronic hepatitis, fatty liver, hepatic cirrhosis, cerebral circulation insufficiency, cerebral ischemia, cerebral infarction, chronic nephritis, chronic pyelonephritis, renal insufficiency, nephrotic syndrome, uremia, and obesity.

In any of the above-mentioned embodiments of the present invention, the plasminogen is administered in combination with one or more other drugs or therapies. In some embodiments, the one or more other drugs comprises a drug for treating hypertension, a drug for treating diabetes mellitus, a drug for treating atherosclerosis, a drug for treating chronic glomerulonephritis, a drug for treating chronic pyelonephritis, a drug for treating nephrotic syndrome, a drug for treating renal insufficiency, a drug for treating uremia, a drug for treating kidney transplantation, a drug for treating fatty liver, a drug for treating hepatic cirrhosis, and a drug for treating obesity. In some embodiments, the other drugs comprise: a hypolipidemic drug, an anti-platelet drug, an antihypertensive drug, a vasodilator, a hypoglycemic drug, an anticoagulant drug, a thrombolytic drug, a hepatoprotective drug, an anti-arrhythmia drug, a cardiotonic drug, a diuretic drug, an anti-infective drug, an antiviral drug, an immunomodulatory drug, an inflammatory regulatory drug, an anti-tumor drug, a hormone drug, and thyroxine. In some further embodiments, the drugs comprise hypolipidemic drugs: statins; fibrates; niacin; cholestyramine; clofibrate; unsaturated fatty acids such as Yishouning, Xuezhiping, and Xinmaile; and alginic sodium diester; anti-platelet drugs: aspirin; dipyridamole; clopidogrel; and cilostazol; vasodilators: hydralazine; nitroglycerin, and isosorbide dinitrate; sodium nitroprusside; α1-receptor blockers such as prazosin; α-receptor blockers such as phentolamine; β2-receptor stimulants such as salbutamol; captopril, enalapril; nifedipine, diltiazem; and salbutamol, loniten, prostaglandin, and atrial natriuretic peptide; thrombolytic drugs: urokinase, and streptokinase; tissue-type plasminogen activators; single chain urokinase-type plasminogen activators; and a TNK tissue-type plasminogen activator; and anticoagulant drugs: heparin; enoxaparin; nadroparin; and bivalirudin.

In any of the above-mentioned embodiments of the present invention, the plasminogen may have at least 75%, 80%, 85%, 90%, 95%, 96%, 97%, 98% or 99% sequence identity with SEQ ID No. 2, 6, 8, 10 or 12, and still have the activity of plasminogen. In some embodiments, the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No. 2, 6, 8, 10 or 12, and still has the activity of plasminogen.

In some embodiments, the plasminogen is a protein that comprises a plasminogen active fragment and still has the activity of plasminogen. In some embodiments, the plasminogen is selected from Glu-plasminogen, Lys-plasminogen, mini-plasminogen, micro-plasminogen, delta-plasminogen or their variants that retain the plasminogen activity. In some embodiments, the plasminogen is a natural or synthetic human plasminogen, or a variant or fragment thereof that still retains the plasminogen activity. In some embodiments, the plasminogen is an ortholog of human plasminogen from a primate or a rodent, or a variant or fragment thereof that still retains the plasminogen activity. In some embodiments, the amino acids of the plasminogen are as shown in SEQ ID No. 2, 6, 8, 10 or 12. In some embodiments, the plasminogen is a natural human plasminogen.

In some embodiments, the subject is a human. In some embodiments, the subject is lack of or deficient in plasminogen. In some embodiments, the lack or deficiency is congenital, secondary and/or local.

In some embodiments, the pharmaceutical composition comprises a pharmaceutically acceptable carrier and the plasminogen for use in the above-mentioned method. In some embodiments, the kit may be a preventive or therapeutic kit comprising: (i) the plasminogen for use in the above-mentioned method, and (ii) a means for delivering the plasminogen to the subject. In some embodiments, the means is a syringe or a vial. In some embodiments, the kit further comprises a label or an instruction for use indicating the administration of the plasminogen to the subject to implement any one of the above-mentioned methods.

In some embodiments, the article of manufacture comprising: a container comprising a label; and (i) the plasminogen for use in the above-mentioned methods or a pharmaceutical composition comprising the plasminogen, wherein the label indicates the administration of the plasminogen or the composition to the subject to implement any one of the above-mentioned methods.

In some embodiments, the kit or the article of manufacture further comprises one or more additional means or containers containing other drugs. In some embodiments, the other drugs are selected from a group of: a hypolipidemic drug, an anti-platelet drug, an antihypertensive drug, a vasodilator, a hypoglycemic drug, an anticoagulant drug, a thrombolytic drug, a hepatoprotective drug, an anti-arrhythmia drug, a cardiotonic drug, a diuretic drug, an anti-infective drug, an antiviral drug, an immunomodulatory drug, an inflammatory regulatory drug, an anti-tumor drug, a hormone drug, and thyroxine.

In some embodiments of the above-mentioned method, the plasminogen is administered by systemic or topical route, preferably by the following routes: intravenous, intramuscular, and subcutaneous administration of plasminogen for treatment. In some embodiments of the above-mentioned method, the plasminogen is administered in combination with a suitable polypeptide carrier or stabilizer. In some embodiments of the above-mentioned method, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily.

The present invention explicitly encompasses all the combinations of technical features belonging to the embodiments of the present invention, and these combined technical solutions have been explicitly disclosed in the present application, as if the above-mentioned technical solutions were individually and explicitly disclosed. In addition, the present invention also explicitly encompasses all the combinations between various embodiments and elements thereof, and the combined technical solutions are explicitly disclosed herein.

DETAILED DESCRIPTION OF EMBODIMENTS

Definition

The "fat metabolism disorder" of the present invention, also known as "abnormal fat metabolism" and "lipodystrophy", is the generic term for the clinical or pathological manifestations caused by the abnormality, disorder or dysfunction of fat metabolism. "Fat metabolism disorder", "abnormal fat metabolism", and "lipodystrophy" are used interchangeably herein. "Fat metabolism", "lipid metabolism", and "metabolism of lipids" are used interchangeably in the present invention.

"A fat metabolism disorder-related condition" is the generic term for the conditions related to fat metabolism disorder. The expression "related" may be etiology-, pathogenesis-, pathogenic manifestation-, clinical symptom- and/or therapeutic principle-related.

"Blood lipid" is the generic term for triglycerides, cholesterol and phospholipids. Lipoprotein is a globular macromolecular complex composed of apolipoproteins and blood lipids. Since lipoprotein is composed of different components, cholesterol and triglycerides, at different densities, it is divided into 5 categories: chylomicron (CM), very low-density lipoprotein (VLDL), intermediate density lipoprotein (IDL), low-density lipoprotein (LDL), and high-density lipoprotein (HDL). According to the blood lipid risk level, the most common clinical types of dyslipoproteinemia are: hypercholesterolemia, hypertriglyceridemia, combined hyperlipemia, and hypo-high-density lipoproteinemia. Secondary dyslipidemia is commonly found in diabetes mellitus, hypothyroidism, nephrotic syndrome, kidney transplantation, a severe liver disease, an obstructive biliary tract disease, obesity, drinking, and drug therapy such as oestrogen therapy, etc. Primary dyslipidemia can be considered if secondary dyslipidemia can be ruled out.

"Hyperlipemia" refers to a pathological condition in which blood lipid components such as cholesterol, triglycerides, phospholipids and non-lipidated fatty acids are elevated in plasma.

"A hyperlipemia-related condition" refers to a condition of which etiology, pathogenesis, pathogenic manifestations, clinical symptoms and/or therapeutic principle are related to hyperlipemia. Preferably, the condition includes but is not limited to diabetes mellitus, hypertension, atherosclerosis, coronary heart disease, angina pectoris, myocardial infarction, arrhythmia, chronic hepatitis, fatty liver, hepatic cirrhosis, cerebral circulation insufficiency, cerebral ischemia, cerebral infarction, chronic nephritis, chronic pyelonephritis, renal insufficiency, nephrotic syndrome, uremia, and obesity.

Abnormalities of one or several lipids in plasma due to abnormal fat metabolism or turnover are referred to as "hyperlipemia", "hyperlipidemia" or "dyslipidemia".

Lipids are insoluble or slightly soluble in water, and must bind to proteins to form lipoproteins to function in the blood circulation. Therefore, hyperlipemia is often a reflection of "hyperlipoproteinemia".

The "hyperlipemia-related condition" of the present invention is also known as "hyperlipidemia-related condition" and "hyperlipoproteinemia-related condition".

"Obesity" or "adiposis" refers to excessive accumulation and/or abnormal distribution of fat in the body. Common indexes for determining obesity or adiposis are body mass index (BMI) and waist circumference (WC). Currently, the classification criteria of the World Health Organization are overweight with BMI≥25 kg·m$^2$ and obesity with BMI≥30 kg·m$^2$. However, the index varies slightly depending on country, region and race. For instance, the Guidelines for the Prevention and Control of Overweight and Obesity in Chinese Adults (Trial) in 2003 states that the case of BMI≥24 kg·m$^2$ should belong to overweight in Chinese adults and the case of BMI≥28 kg·m$^2$ should belong to obesity. From the above-mentioned ranking of "obesity" and "overweight", overweight and obesity reflect different degrees. Obesity or adiposis in the claims and description of the present invention encompasses the meaning of "overweight". The "obesity", "adiposisand" and "overweight" of the present invention can be excessive weight gain caused by various causes, such as simply by eating.

The experiment of the present invention proves that plasminogen can improve the abnormal or excessive fat deposition in the organs in the body, around the organs, in the abdominal cavity, etc. Therefore, it can be used as a weight-loss drug to treat obesity or overweight, and reduce fat and body weight.

The present invention relates to plasminogen used as a weight-loss drug, or a pharmaceutical composition, a kit or an article of manufacture comprising plasminogen. The plasminogen of the present invention can be used as a food additive in foods or drinks, in addition to being used as a drug. The plasminogen of the present invention can also be used in beauty and weight-loss products for weight loss. Therefore, the plasminogen of the present invention is administered to a subject in need of losing weight or reducing weight in various convenient forms.

Plasmin is a key component of the plasminogen activation system (PA system). It is a broad-spectrum protease that can hydrolyze several components of the extracellular matrix (ECM), including fibrin, gelatin, fibronectin, laminin, and proteoglycan [9]. In addition, plasmin can activate some pro-matrix metalloproteinases (pro-MMPs) to form active matrix metalloproteinases (MMPs). Therefore, plasmin is considered to be an important upstream regulator of extracellular proteolysis [10,11]. Plasmin is formed by the proteolysis of plasminogen by two physiological PAs: tissue plasminogen activator (tPA) or urokinase-type plasminogen activator (uPA). Due to the relatively high level of plasminogen in plasma and other body fluids, it is traditionally believed that the regulation of the PA system is primarily achieved through the levels of PA synthesis and activity. The synthesis of PA system components is strictly regulated by different factors, such as hormones, growth factors and cytokines. In addition, there are also specific physiological inhibitors of plasmin and PAs. The main inhibitor of plasmin is α2-antiplasmin. The activity of PAs is simultaneously inhibited by the plasminogen activator inhibitor-1 (PAI-1) of uPA and tPA and regulated by the plasminogen activator inhibitor-2 (PAI-2) that primarily inhibits uPA. There are uPA-specific cell surface receptors (uPARs) that have direct hydrolytic activity on certain cell surfaces [12,13].

Plasminogen (plg) is a single-stranded glycoprotein composed of 791 amino acids and has a molecular weight of about 92 kDa [14,15]. Plasminogen is mainly synthesized in the liver and is abundantly present in the extracellular fluid. The content of plasminogen in plasma is about 2 μM. Therefore, plasminogen is a huge potential source of proteolytic activity in tissues and body fluids [16,17] Plasminogen exists in two molecular forms: glutamic acid-plasminogen (Glu-plasminogen) and lysine-plasminogen (Lys-plasminogen). The naturally secreted and uncleaved forms of plasminogen have an amino-terminal (N-terminal) glutamic acid and are therefore referred to as glutamic acid-plasminogen. However, in the presence of plasmin, glutamic acid-plasminogen is hydrolyzed to lysine-plasminogen at Lys76-Lys77. Compared with glutamic acid-plasminogen, lysine-plasminogen has a higher affinity for fibrin and can be activated by PAs at a higher rate. The Arg560-Val561 peptide bond between these two forms of plasminogen can be cleaved by uPA or tPA, resulting in the formation of plasmin as a disulfide-linked double-strand protease [18]. The amino-terminal portion of plasminogen contains five homotrimeric rings, i.e., the so-called kringles, and the carboxy-terminal portion contains a protease domain. Some kringles contain lysine-binding sites that mediate the specific interaction of plasminogen with fibrin and its inhibitor α2-AP. A newly discovered plasminogen is a 38 kDa fragment, comprising kringles 1-4, is a potent inhibitor of angiogenesis. This fragment is named as angiostatin and can be produced by proteolysis of plasminogen by several proteases.

The main substrate of plasmin is fibrin, and the dissolution of fibrin is the key to prevent pathological thrombosis [19]. Plasmin also has substrate specificity for several components of ECM, including laminin, fibronectin, proteoglycan and gelatin, indicating that plasmin also plays an important role in ECM remodeling [15,20,21]. Indirectly, plasmin can also degrade other components of ECM by converting certain protease precursors into active proteases, including MMP-1, MMP-2, MMP-3 and MMP-9. Therefore, it has been proposed that plasmin may be an important upstream regulator of extracellular proteolysis [22]. In addition, plasmin has the ability to activate certain potential forms of growth factors [23-25]. In vitro, plasmin can also hydrolyze components of the complement system and release chemotactic complement fragments.

"Plasmin" is a very important enzyme that exists in the blood and can hydrolyze fibrin clots into fibrin degradation products and D-dimers.

"Plasminogen" is the zymogenic form of plasmin, and based on the sequence in the swiss prot and calculated from the amino acid sequence (SEQ ID No. 4) of the natural human plasminogen containing a signal peptide, is a glycoprotein composed of 810 amino acids, which has a molecular weight of about 90 kD and is synthesized mainly in the liver and capable of circulating in the blood; and the cDNA sequence encoding this amino acid sequence is as shown in SEQ ID No. 3. Full-length plasminogen contains seven domains: a C-terminal serine protease domain, an N-terminal Pan Apple (PAp) domain and five Kringle domains (Kringles 1-5). Referring to the sequence in the swiss prot, the signal peptide comprises residues Met1-Gly19, PAp comprises residues Glu20-Val198, Kringle 1 comprises residues Cys103-Cys181, Kringle 2 comprises residues Glu184-Cys262, Kringle 3 comprises residues Cys275-Cys352, Kringle 4 comprises residues Cys377-Cys454, and Kringle 5 comprises residues Cys481-Cys560. According to the NCBI data, the serine protease domain comprises residues Val581-Arg804.

Glu-plasminogen is a natural full-length plasminogen and is composed of 791 amino acids (without a signal peptide of 19 amino acids); the cDNA sequence encoding this sequence is as shown in SEQ ID No. 1; and the amino acid sequence is as shown in SEQ ID No. 2. In vivo, Lys-plasminogen, which is formed by hydrolysis of amino acids at positions 76-77 of Glu-plasminogen, is also present, as shown in SEQ ID No.6; and the cDNA sequence encoding this amino acid sequence is as shown in SEQ ID No.5. δ-plasminogen is a fragment of full-length plasminogen that lacks the structure of Kringle 2-Kringle 5 and contains only Kringle 1 and the serine protease domain [26,27]. The amino acid sequence (SEQ ID No. 8) of δ-plasminogen has been reported in the literature [27], and the cDNA sequence encoding this amino acid sequence is as shown in SEQ ID No. 7. Mini-plasminogen is composed of Kringle 5 and the serine protease domain, and has been reported in the literature to comprise residues Val443-Asn791 (with the Glu residue of the Glu-plasminogen sequence that does not contain a signal peptide as the starting amino acid) [28]; the amino acid sequence is as shown in SEQ ID No. 10; and the cDNA sequence encoding this amino acid sequence is as shown in SEQ ID No. 9. Micro-plasminogen comprises only the serine protease domain, the amino acid sequence of which has been reported in the literature to comprise residues Ala543-Asn791 (with the Glu residue of the Glu-plasminogen sequence that does not contain a signal peptide as the starting amino acid) [29], and the sequence of which has been also reported in patent document CN 102154253 A to comprise residues Lys531-Asn791 (with the Glu residue of the Glu-plasminogen sequence that does not contain a signal peptide as the starting amino acid) (the sequence in this patent application refers to the patent document CN 102154253 A); the amino acid sequence is as shown in SEQ ID No. 12; and the cDNA sequence encoding this amino acid sequence is as shown in SEQ ID No. 11.

In the present invention, "plasmin" is used interchangeably with "fibrinolysin" and "fibrinoclase", and the terms have the same meaning; and "plasminogen" is used interchangeably with "plasminogen" and "fibrinoclase zymogen", and the terms have the same meaning.

In the present application, the meaning of "lack" in plasminogen is that the content or activity of plasminogen in the body of a subject is lower than that of a normal person, which is low enough to affect the normal physiological function of the subject; and the meaning of "deficiency" in plasminogen is that the content or activity of plasminogen in the body of a subject is significantly lower than that of a normal person, or even the activity or expression is extremely small, and only through exogenous supply can the normal physiological function be maintained.

Those skilled in the art can understand that all the technical solutions of the plasminogen of the present invention are suitable for plasmin. Therefore, the technical solutions described in the present invention cover plasminogen and plasmin.

In the course of circulation, plasminogen is in a closed, inactive conformation, but when bound to thrombi or cell surfaces, it is converted into an active plasmin in an open conformation under the mediation of a plasminogen activator (PA). The active plasmin can further hydrolyze the fibrin clots to fibrin degradation products and D-dimers, thereby dissolving the thrombi. The PAp domain of plasminogen comprises an important determinant that maintains plasminogen in an inactive, closed conformation, and the KR domain is capable of binding to lysine residues present on receptors and substrates. A variety of enzymes that can serve as plasminogen activators are known, including: tissue plasminogen activator (tPA), urokinase plasminogen activator (uPA), kallikrein, coagulation factor XII (Hagmann factor), and the like.

"Plasminogen active fragment" refers to an active fragment in the plasminogen protein that is capable of binding to a target sequence in a substrate and exerting the proteolytic function. The technical solutions of the present invention involving plasminogen encompass technical solutions in which plasminogen is replaced with a plasminogen active fragment. The plasminogen active fragment of the present invention is a protein comprising a serine protease domain of plasminogen. Preferably, the plasminogen active fragment of the present invention comprises SEQ ID No.14, or an amino acid sequence having an amino acid sequence identity of at least 80%, 90%, 95%, 96%, 97%, 98% or 99% with SEQ ID No.14. Therefore, plasminogen of the present invention comprises a protein containing the plasminogen active fragment and still having the plasminogen activity.

At present, methods for determining plasminogen and its activity in blood include: detection of tissue plasminogen activator activity (t-PAA), detection of tissue plasminogen activator antigen (t-PAAg) in plasma, detection of tissue plasminogen activity (plgA) in plasma, detection of tissue plasminogen antigen (plgAg) in plasma, detection of activity of the inhibitor of tissue plasminogen activators in plasma, detection of inhibitor antigens of tissue plasminogen activators in plasma and detection of plasmin-anti-plasmin (PAP) complex in plasma. The most commonly used detection method is the chromogenic substrate method: streptokinase (SK) and a chromogenic substrate are added to a test plasma, the PLG in the test plasma is converted into PLM by the action of SK, PLM acts on the chromogenic substrate, and then it is determined that the increase in absorbance is directly proportional to plasminogen activity using a spectrophotometer. In addition, plasminogen activity in blood can also be determined by immunochemistry, gel electrophoresis, immunonephelometry, radioimmuno-diffusion and the like.

"Orthologues or orthologs" refer to homologs between different species, including both protein homologs and DNA homologs, and are also known as orthologous homologs and vertical homologs. The term specifically refers to proteins or genes that have evolved from the same ancestral gene in different species. The plasminogen of the present invention includes human natural plasminogen, and also includes orthologues or orthologs of plasminogens derived from different species and having plasminogen activity.

"Conservatively substituted variant" refers to one in which a given amino acid residue is changed without altering the overall conformation and function of the protein or enzyme, including, but not limited to, replacing an amino acid in the amino acid sequence of the parent protein by an amino acid with similar properties (such as acidity, alkalinity, hydrophobicity, etc.). Amino acids with similar properties are well known. For example, arginine, histidine and lysine are hydrophilic basic amino acids and are interchangeable. Similarly, isoleucine is a hydrophobic amino acid that can be replaced by leucine, methionine or valine. Therefore, the similarity of two proteins or amino acid sequences with similar functions may be different. For example, the similarity (identity) is 70%-99% based on the MEGALIGN algorithm. "Conservatively substituted variant" also includes a polypeptide or enzyme having amino acid identity of 60% or more, preferably 75% or more, more preferably 85% or more, even more preferably 90% or more as determined by the BLAST or FASTA algorithm, and having the same or substantially similar properties or functions as the natural or parent protein or enzyme.

"Isolated" plasminogen refers to the plasminogen protein that is isolated and/or recovered from its natural environment. In some embodiments, the plasminogen will be purified (1) to a purity of greater than 90%, greater than 95% or greater than 98% (by weight), as determined by the Lowry method, such as more than 99% (by weight); (2) to a degree sufficiently to obtain at least 15 residues of the N-terminal or internal amino acid sequence using a spinning cup sequenator; or (3) to homogeneity, which is determined by sodium dodecyl sulfate-polyacrylamide gel electrophoresis (SDS-PAGE) under reducing or non-reducing conditions using Coomassie blue or silver staining. Isolated plasminogen also includes plasminogen prepared from recombinant cells by bioengineering techniques and separated by at least one purification step.

The terms "polypeptide", "peptide" and "protein" are used interchangeably herein and refer to polymeric forms of amino acids of any length, which may include genetically encoded and non-genetically encoded amino acids, chemically or biochemically modified or derivatized amino acids, and polypeptides having modified peptide backbones. The term includes fusion proteins, including, but not limited to, fusion proteins having heterologous amino acid sequences, fusions having heterologous and homologous leader sequences (with or without N-terminal methionine residues); and the like.

The "percent amino acid sequence identity (%)" with respect to the reference polypeptide sequence is defined as the percentage of amino acid residues in the candidate sequence identical to the amino acid residues in the reference polypeptide sequence when a gap is introduced as necessary to achieve maximal percent sequence identity and no conservative substitutions are considered as part of sequence identity. The comparison for purposes of determining percent amino acid sequence identity can be achieved in a variety of ways within the skill in the art, for example using publicly available computer softwares, such as BLAST, BLAST-2, ALIGN or Megalign (DNASTAR) software. Those skilled in the art can determine appropriate parameters for aligning sequences, including any algorithm needed to achieve the maximum comparison over the full length of the sequences being compared. However, for purposes of the present invention, the percent amino acid sequence identity value is generated using the sequence comparison computer program ALIGN-2.

In the case of comparing amino acid sequences using ALIGN-2, the % amino acid sequence identity of a given amino acid sequence A relative to a given amino acid sequence B (or may be expressed as a given amino acid sequence A having or containing a certain % amino acid sequence identity relative to, with or for a given amino acid sequence B) is calculated as follows:

fraction $X/Y \times 100$ wherein X is the number of identically matched amino acid residues scored by the sequence alignment program ALIGN-2 in the alignment of A and B using the program, and wherein Y is the total number of amino acid residues in B. It will be appreciated that where the length of amino acid sequence A is not equal to the length of amino acid sequence B, the % amino acid sequence identity of A relative to B will not be equal to the % amino acid sequence identity of B relative to A. Unless specifically stated otherwise, all the % amino acid sequence identity values used herein are obtained using the ALIGN-2 computer program as described in the previous paragraph.

As used herein, the terms "treatment" and "treating" refer to obtaining a desired pharmacological and/or physiologic effect. The effect may be complete or partial prevention of a disease or its symptoms and/or partial or complete cure of the disease and/or its symptoms, and includes: (a) prevention of the disease from developing in a subject that may have a predisposition to the disease but has not been diagnosed as having the disease; (b) suppression of the disease, i.e., blocking its formation; and (c) alleviation of the disease and/or its symptoms, i.e., eliminating the disease and/or its symptoms.

The terms "individual", "subject" and "patient" are used interchangeably herein and refer to mammals, including, but not limited to, murine (rats and mice), non-human primates, humans, dogs, cats, hoofed animals (e.g., horses, cattle, sheep, pigs, goats) and so on.

"Therapeutically effective amount" or "effective amount" refers to an amount of plasminogen sufficient to achieve the prevention and/or treatment of a disease when administered to a mammal or another subject to treat the disease. The "therapeutically effective amount" will vary depending on the plasminogen used, the severity of the disease and/or its symptoms, as well as the age, body weight of the subject to be treated, and the like.

Preparation of the Plasminogen of the Present Invention

Plasminogen can be isolated and purified from nature for further therapeutic uses, and can also be synthesized by standard chemical peptide synthesis techniques. When chemically synthesized, a polypeptide can be subjected to liquid or solid phase synthesis. Solid phase polypeptide synthesis (SPPS) is a method suitable for chemical synthesis of plasminogen, in which the C-terminal amino acid of a sequence is attached to an insoluble support, followed by the sequential addition of the remaining amino acids in the sequence. Various forms of SPPS, such as Fmoc and Boc, can be used to synthesize plasminogen. Techniques for solid phase synthesis are described in Barany and Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963); Stewart et al. Solid Phase Peptide Synthesis, 2nd ed. Pierce Chem. Co., Rockford, Ill. (1984); and Ganesan A. 2006 Mini Rev. Med Chem. 6:3-10 and Camarero J A et al. 2005 Protein Pept Lett. 12:723-8. Briefly, small insoluble porous beads are treated with a functional unit on which a peptide chain is constructed. After repeated cycles of coupling/deprotection, the attached solid phase free N-terminal amine is coupled to a single N-protected amino acid unit. This unit is then deprotected to expose a new N-terminal amine that can be attached to another amino acid. The peptide remains immobilized on the solid phase before it is cut off.

Standard recombinant methods can be used to produce the plasminogen of the present invention. For example, a nucleic acid encoding plasminogen is inserted into an expression vector, so that it is operably linked to a regulatory sequence in the expression vector. Expression regulatory sequence includes, but is not limited to, promoters (e.g., naturally associated or heterologous promoters), signal sequences, enhancer elements and transcription termination sequences. Expression regulation can be a eukaryotic promoter system in a vector that is capable of transforming or transfecting eukaryotic host cells (e.g., COS or CHO cells). Once the vector is incorporated into a suitable host, the host is maintained under conditions suitable for high-level expression of the nucleotide sequence and collection and purification of plasminogen.

A suitable expression vector is usually replicated in a host organism as an episome or as an integral part of the host chromosomal DNA. In general, an expression vector contains a selective marker (e.g., ampicillin resistance, hygromycin resistance, tetracycline resistance, kanamycin resistance or neomycin resistance) to facilitate detection of those exogenous cells transformed with a desired DNA sequence.

*Escherichia coli* is an example of prokaryotic host cells that can be used to clone a polynucleotide encoding the subject antibody. Other microbial hosts suitable for use include *Bacillus*, for example, *Bacillus subtilis* and other species of enterobacteriaceae (such as *Salmonella* spp. and *Serratia* spp.), and various *Pseudomonas* spp. In these prokaryotic hosts, expression vectors can also be generated which will typically contain an expression control sequence (e.g., origin of replication) that is compatible with the host cell. In addition, there will be many well-known promoters, such as the lactose promoter system, the tryptophan (trp) promoter system, the beta-lactamase promoter system or the promoter system from phage lambda. Optionally in the case of manipulation of a gene sequence, a promoter will usually control expression, and has a ribosome binding site sequence and the like to initiate and complete transcription and translation.

Other microorganisms, such as yeast, can also be used for expression. *Saccharomyces* (e.g., *S. cerevisiae*) and *Pichia* are examples of suitable yeast host cells, in which a suitable vector has an expression control sequence (e.g., promoter), an origin of replication, a termination sequence and the like, as required. A typical promoter comprises 3-phosphoglycerate kinase and other glycolytic enzymes. Inducible yeast promoters specifically include promoters derived from alcohol dehydrogenase, isocytochrome C, and enzymes responsible for maltose and galactose utilization.

In addition to microorganisms, mammalian cells (e.g., mammalian cells cultured in cell culture in vitro) can also be used to express and generate the anti-Tau antibody of the present invention (e.g., a polynucleotide encoding a subject anti-Tau antibody). See Winnacker, From Genes to Clones, VCH Publishers, N.Y., N.Y. (1987). Suitable mammalian host cells include CHO cell lines, various Cos cell lines, HeLa cells, myeloma cell lines and transformed B cells or hybridomas. Expression vectors for these cells may comprise an expression control sequence, such as an origin of replication, promoter and enhancer (Queen et al. Immunol. Rev. 89:49 (1986)), as well as necessary processing information sites, such as a ribosome binding site, RNA splice site, polyadenylation site and transcription terminator sequence. Examples of suitable expression control sequences are promoters derived from white immunoglobulin gene, SV40, adenovirus, bovine papilloma virus, cytomegalovirus and the like. See Co et al. J. Immunol. 148:1149 (1992).

Once synthesized (chemically or recombinantly), the plasminogen of the present invention can be purified according to standard procedures in the art, including ammonium sulfate precipitation, affinity column, column chromatography, high performance liquid chromatography (HPLC), gel electrophoresis and the like. The plasminogen is substantially pure, e.g., at least about 80% to 85% pure, at least about 85% to 90% pure, at least about 90% to 95% pure, or 98% to 99% pure or purer, for example free of contaminants such as cell debris, macromolecules other than the subject antibody and the like.

Pharmaceutical Formulations

A therapeutic formulation can be prepared by mixing plasminogen of a desired purity with an optional pharmaceutical carrier, excipient or stabilizer (Remington's Pharmaceutical Sciences, 16th edition, Osol, A. ed. (1980)) to form a lyophilized preparation or an aqueous solution. Acceptable carriers, excipients and stabilizers are non-toxic to the recipient at the dosages and concentrations employed, and include buffers, such as phosphates, citrates and other organic acids; antioxidants, including ascorbic acid and methionine; preservatives (e.g., octadecyl dimethyl benzyl ammonium chloride; hexane chloride diamine; benzalkonium chloride and benzethonium chloride; phenol, butanol or benzyl alcohol; alkyl p-hydroxybenzoates, such as methyl or propyl p-hydroxybenzoate; catechol; resorcinol; cyclohexanol; 3-pentanol; and in-cresol); low molecular weight polypeptides (less than about 10 residues); proteins, such as serum albumin, gelatin or immunoglobulins; hydrophilic polymers, such as polyvinylpyrrolidone; amino acids, such as glycine, glutamine, asparagine, histidine, arginine or lysine; monosaccharides, disaccharides and other carbohydrates, including glucose, mannose or dextrins; chelating agents, such as EDTA; sugars, such as sucrose, mannitol, fucose or sorbitol; salt-forming counterions, such as sodium; metal complexes (e.g., zinc-protein complexes); and/or nonionic surfactants, such as TWEEN™, PLURONICS™ or polyethylene glycol (PEG). Preferred lyophilized anti-VEGF antibody formulations are described in WO 97/04801, which is incorporated herein by reference.

The formulations of the invention may also comprise one or more active compounds required for the particular disorder to be treated, preferably those that are complementary in activity and have no side effects with one another, for example anti-hypertensive drugs, anti-arrhythmic drugs, drugs for treating diabetes mellitus, and the like.

The plasminogen of the present invention may be encapsulated in microcapsules prepared by techniques such as coacervation or interfacial polymerization, for example, it may be incorporated in a colloid drug delivery system (e.g., liposomes, albumin microspheres, microemulsions, nanoparticles and nanocapsules), or incorporated in hydroxymethylcellulose or gel-microcapsules and poly-(methyl methacrylate) microcapsules in macroemulsions. These techniques are disclosed in Remington's Pharmaceutical Sciences, 16th edition, Osol, A. Ed. (1980).

The plasminogen of the present invention for in vivo administration must be sterile. This can be easily achieved by filtration through a sterile filtration membrane before or after freeze drying and reconstitution.

The plasminogen of the present invention can be prepared into a sustained-release preparation. Suitable examples of sustained-release preparations include solid hydrophobic polymer semi-permeable matrices having a shape and containing glycoproteins, such as films or microcapsules. Examples of sustained-release matrices include polyesters, hydrogels (e.g., poly(2-hydroxyethyl-methacrylate)) (Langer et al. J. Biomed. Mater. Res., 15: 167-277 (1981); and Langer, Chem. Tech., 12:98-105 (1982)), or poly(vinyl alcohol), polylactides (U.S. Pat. No. 3,773,919, and EP 58,481), copolymer of L-glutamic acid and □ ethyl-L-glutamic acid (Sidman et al. Biopolymers 22:547 (1983)), nondegradable ethylene-vinyl acetate (Langer et al. supra), or degradable lactic acid-glycolic acid copolymers such as Lupron Depot™ (injectable microspheres composed of lactic acid-glycolic acid copolymer and leuprolide acetate), and poly D-(−)-3-hydroxybutyric acid. Polymers, such as ethylene-vinyl acetate and lactic acid-glycolic acid, are able to persistently release molecules for 100 days or longer, while some hydrogels release proteins for a shorter period of time. A rational strategy for protein stabilization can be designed based on relevant mechanisms. For example, if the aggregation mechanism is discovered to be formation of an intermolecular S—S bond through thio-disulfide interchange, stability is achieved by modifying sulfhydryl residues, lyophilizing from acidic solutions, controlling moisture content, using appropriate additives, and developing specific polymer matrix compositions.

Administration and Dosage

The pharmaceutical composition of the present invention is administered in different ways, for example by intravenous, intraperitoneal, subcutaneous, intracranial, intrathecal, intraarterial (e.g., via carotid), and intramuscular administration.

Preparations for parenteral administration include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, and alcoholic/aqueous solutions, emulsions or suspensions, including saline and buffered media. Parenteral vehicles include sodium chloride solution, Ringer's dextrose, dextrose and sodium chloride, or fixed oils. Intravenous vehicles include liquid and nutrient supplements, electrolyte supplements and the like. Preservatives and other additives may also be present, for example, such as antimicrobial agents, antioxidants, chelating agents and inert gases.

The medical staff will determine the dosage regimen based on various clinical factors. As is well known in the medical field, the dosage of any patient depends on a variety of factors, including the patient's size, body surface area, age, the specific compound to be administered, sex, frequency and route of administration, overall health and other drugs administered simultaneously. The dosage range of the pharmaceutical composition comprising plasminogen of the present invention may be, for example, such as about 0.0001 to 2000 mg/kg, or about 0.001 to 500 mg/kg (such as 0.02 mg/kg, 0.25 mg/kg, 0.5 mg/kg, 0.75 mg/kg, 10 mg/kg and 50 mg/kg) of the subject's body weight daily. For example, the dosage may be 1 mg/kg body weight or 50 mg/kg body weight, or in the range of 1 mg/kg-50 mg/kg, or at least 1 mg/kg. Dosages above or below this exemplary range are also contemplated, especially considering the above factors. The intermediate dosages in the above range are also included in the scope of the present invention. A subject may be administered with such dosages daily, every other day, weekly or based on any other schedule determined by empirical analysis. An exemplary dosage schedule includes 1-10 mg/kg for consecutive days. During administration of the drug of the present invention, the therapeutic effect and safety are required to be assessed real-timely.

Articles of Manufacture or Kits

One embodiment of the present invention relates to an article of manufacture or a kit comprising plasminogen of the present invention or plasmin useful in the treatment of obesity and its related conditions. The article preferably includes a container, label or package insert. Suitable containers include bottles, vials, syringes and the like. The container can be made of various materials, such as glass or plastic. The container contains a composition that is effective to treat the disease or disorder of the present invention and has a sterile access (for example, the container may be an intravenous solution bag or vial containing a plug that can be pierced by a hypodermic injection needle). At least one active agent in the composition is plasminogen/plasmin. The label on or attached to the container indicates that the composition is used to treat the obesity and its related conditions caused by diabetes mellitus according to the present invention. The article may further comprise a second container containing a pharmaceutically acceptable buffer, such as phosphate buffered saline, Ringer's solution and glucose solution. It may further comprise other substances required from a commercial and user perspective, including other buffers, diluents, filters, needles and syringes. In addition, the article comprises a package insert with instructions for use, including, for example, instructions to a user of the composition to administer the plasminogen composition and other drugs to treat an accompanying disease to a patient.

BRIEF DESCRIPTION OF THE DRAWINGS

FIG. 4 shows detection results of blood lipid in high-calorie diet-induced obesity model mice. A represents total cholesterol, B represents low-density lipoprotein, and C represents high-density lipoprotein. The results showed that there were no significant differences in the concentrations of total cholesterol, low-density lipoprotein and high-density lipoprotein among the group administered with plasminogen, the control group administered with vehicle PBS, and the blank control group. It indicates that there is no significant change in blood lipid of high-calorie diet-induced obesity model mice in this experiment.

FIG. 5 shows detection results of serum leptin in high-calorie diet-induced obesity model mice. The results showed that there were no significant differences in the leptin concentration among the group administered with plasminogen, the control group administered with vehicle PBS, and the blank control group. It indicates that there is no significant change in leptin of high-calorie diet-induced obesity model mice in this experiment.

FIG. 6 shows detection results of serum insulin in high-calorie diet-induced obesity model mice. The results showed that there were no significant differences in the insulin concentration among the group administered with plasminogen, the control group administered with vehicle PBS, and the blank control group. It indicates that there is no significant change in insulin of high-calorie diet-induced obesity model mice in this experiment.

EXAMPLES

Example 1. Effect of Plasminogen on the High-Calorie Diet-Induced Obese Mice Model Mouse Model and Grouping Fourteen 8-week-old male C57 mice were randomly divided into two groups based on the body weight, a blank control group of 4 mice and a model group of 10 mice. Mice in the blank control group were fed with a normal maintenance diet; mice in the model group were fed with a high-fat diet containing 45% fat calories (TP23000, Nantong TROPHIC Feed Technology Co., Ltd.) for model establishment for 12 weeks to establish an obesity model [30]. A high-fat diet containing 45% fat calories is herein referred to as a high-calorie diet. After 12 weeks, mice in the model group were weighed and randomly divided into two groups again based on the body weight, 5 mice in each of a group administered with plasminogen and a control group administered with vehicle PBS. Human plasminogen was dissolved in PBS. The mice in the group administered with plasminogen were injected with human plasminogen at a dose of 1 mg/0.1 mL/mouse/day via the tail vein, and the mice in the control group administered with vehicle PBS were injected with an equal volume of PBS via the tail vein. The blank control group received no treatment. The above-mentioned experimental animals were administered for 28 consecutive days (the first day of administration was recorded as Day 1), and treated and detected as follows on Day 29.

Detections and Results

Detection of Body Weights

The above-mentioned experimental animals were weighed on Day 1 and Day 29 to calculate the changes in body weight. The results are shown as the value of the weight on Day 29 minus the weight on Day 1.

Figure 1:
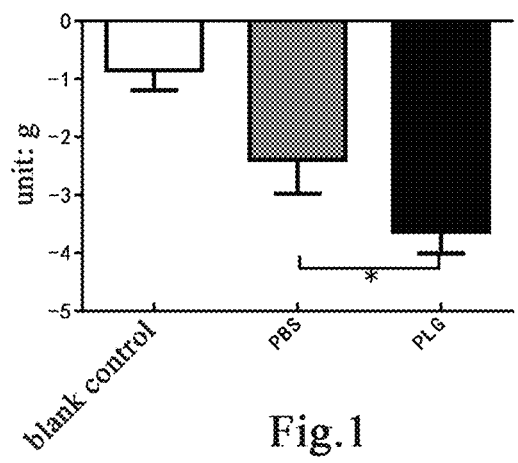
FIG. 1 shows calculation results of body weight changes after administration of plasminogen to high-calorie diet-induced obesity model mice for 28 days. The results are shown as the value of the weight on Day 29 minus the weight on Day 1. The results showed that there was no significant body weight change in the blank control group, the weight loss in the control group administered with vehicle PBS was remarkably lower than that in the group administered with plasminogen, and the statistical difference was significant (* indicates P<0.05). It indicates that plasminogen can promote weight loss in obesity model mice.

The results showed that there was no significant body weight change in the blank control group, the weight loss in the control group administered with vehicle PBS was remarkably less than that in the group administered with plasminogen, and the statistical difference was significant (* indicates P<0.05) (FIG. 1). It indicates that plasminogen can significantly lower the body weight of obesity model mice.

Determination of Body Mass Index

On Day 29, the above-mentioned mice were weighed and measured for body length to calculate the body mass index. Body mass index=Weight (kg)/Body length (in).

Figure 2:
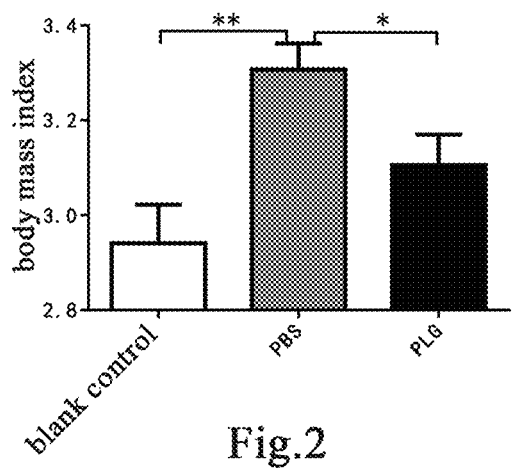
FIG. 2 shows statistical results of the body mass index after administration of plasminogen to high-calorie diet-induced obesity model mice for 28 days. The results showed that the body mass index of mice in the group administered with plasminogen was remarkably lower than that in the control group administered with vehicle PBS, and the statistical difference was significant (* indicates P<0.05, and ** indicates P<0.01); and compared with the control group administered with vehicle PBS, the body mass index of mice in the group administered with plasminogen was closer to that in the blank control group. It indicates that plasminogen can significantly lower the body mass index of obesity model mice, and alleviate obesity.

Body mass index is a commonly used international standard to measure body fatness degree and health of human beings. Body mass index can also be used as an index of fatness degree in obesity model animals [43, 44]. The results showed that the body mass index of mice in the group administered with plasminogen was remarkably lower than that in the control group administered with vehicle PBS, and the statistical difference was significant (* indicates P<0.05); and compared with the control group administered with vehicle PBS, the body mass index of mice in the group administered with plasminogen was closer to that in the blank control group (FIG. 2). It indicates that plasminogen can significantly lower the body mass index of obesity model mice, and alleviate obesity.

Determination of Lee's Index

On Day 29, the above-mentioned mice were weighed and measured for body length to calculate the Lee's index.

$$\text{Lee's index} = \sqrt[3]{\text{Body weight (g)}}/\text{Body length (cm)}.$$

Body Weight(g)

Figure 3:
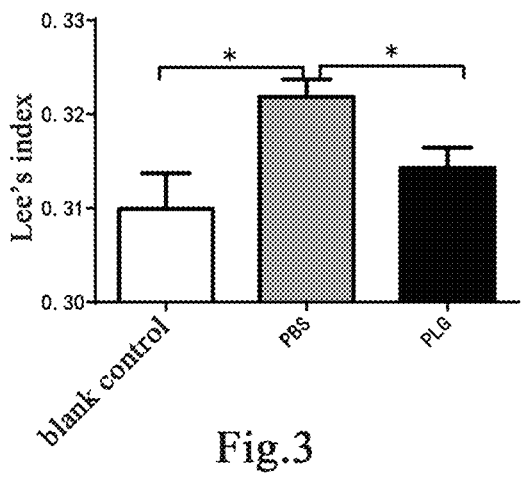
FIG. 3 shows statistical results of the Lee's index after administration of plasminogen to high-calorie diet-induced obesity model mice for 28 days. The results showed that the Lee's index of mice in the group administered with plasminogen was remarkably lower than that in the control group administered with vehicle PBS, and the statistical difference was significant (* indicates P<0.05); and compared with the control group administered with vehicle PBS, the Lee's index of mice in the group administered with plasminogen was closer to that in the blank control group. It indicates that plasminogen can significantly lower the Lee's index of obesity model mice, and alleviate obesity.

Lee's index is an effective index for reflecting the degree of obesity [31-32] The results showed that the Lee's index of mice in the group administered with plasminogen was remarkably lower than that in the control group administered with vehicle PBS, and the statistical difference was significant (* indicates P<0.05); and compared with the control group administered with vehicle PBS, the Lee's index of mice in the group administered with plasminogen was closer to that in the blank control group (FIG. 3). It indicates that plasminogen can significantly lower the Lee's index of obesity model mice, and alleviate obesity.

Detection of Blood Lipid Levels

On Day 29, the blood was collected from removed eyeballs in the above-mentioned model mice, and centrifuged to obtain a supernatant, which was detected for concentrations of serum total cholesterol, low-density lipoprotein, and high-density lipoprotein using the serum total cholesterol, low-density lipoprotein, and high-density lipoprotein detection kits (Nanjing Jiancheng Bioengineering Institute, Cat #A111-1, A113-1, and A112-1) according to the method of the corresponding kit.

The results showed that there were no significant differences in the concentrations of total cholesterol (FIG. 4A), low-density lipoprotein (FIG. 4B) and high-density lipoprotein (FIG. 4C) among the group administered with plasminogen, the control group administered with vehicle PBS, and the blank control group. It indicates that there is no significant change in blood lipid of high-calorie diet-induced obesity model mice in this experiment.

Detection of Serum Leptin Levels

The leptin level in the above-mentioned serum was detected using a serum leptin detection kit (Nanjing Jiancheng Bioengineering Institute, Cat #H174) according to the method of the detection kit.

The results showed that there were no significant differences in the leptin concentration among the group administered with plasminogen, the control group administered with vehicle PBS, and the blank control group (FIG. 5). It indicates that there is no significant change in leptin of high-calorie diet-induced obesity model mice in this experiment.

Leptin (LP) is a hormone secreted by an adipose tissue. Previously, it is generally believed that it will be involved in the regulation of sugar, fat and energy metabolisms after entering the blood circulation, prompting the body to reduce food intake, to increase energy release, to inhibit the synthesis of adipose cells, and thus to reduce body weight. However, some obese individuals have leptin resistance and an elevated leptin level in blood [34]. Relevant studies showed that db/db mice had leptin resistance, and serum leptin levels were significantly elevated [35-36].

Detection of Serum Insulin Levels

The insulin level in the above-mentioned serum was detected using a serum insulin detection kit (Nanjing Jiancheng Bioengineering Institute, Cat #H174) according to the method of the detection kit.

The results showed that there were no significant differences in the insulin concentration among the group administered with plasminogen, the control group administered with vehicle PBS, and the blank control group (FIG. 6). It indicates that there is no significant change in insulin of high-calorie diet-induced obesity model mice in this experiment.

Detection of Abdominal Fat Contents

On Day 29, the above-mentioned mice were weighed and sacrificed to weigh the abdominal fat. Abdominal fat coefficient (%)=(Abdominal fat mass/Body weight)*100.

Figure 7:
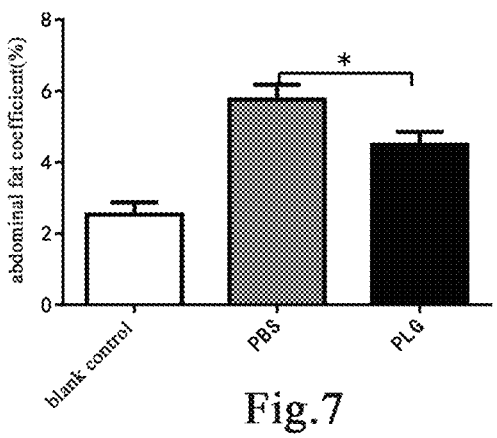
FIG. 7 shows statistical results of the abdominal fat coefficient after administration of plasminogen to high-calorie diet-induced obesity model mice for 28 days. The results showed that the abdominal fat coefficient of mice in the group administered with plasminogen was remarkably lower than that in the control group administered with vehicle PBS, and the statistical difference was significant (* indicates P<0.05); and compared with the control group administered with vehicle PBS, the abdominal fat content of mice in the group administered with plasminogen was closer to that in the blank control group. It indicates that plasminogen can significantly reduce abdominal fat deposition in obesity model mice.

The results showed that the abdominal fat coefficient of mice in the group administered with plasminogen was remarkably lower than that in the control group administered with vehicle PBS with a significant statistical difference (* indicates P<0.05), and was close to the fat coefficient of mice in the blank control group (FIG. 7). It indicates that plasminogen can significantly reduce abdominal fat deposition in obesity model mice.

Detection of Abdominal Subcutaneous Fat Vacuolar Area

The above-mentioned mice were sacrificed on Day 29. The abdominal fat was fixed in 4% paraformaldehyde for 24 to 48 hours. The fixed tissue samples were paraffin-embedded after dehydration with alcohol gradient and permeabilization with xylene. The tissue sections were 4 μm thick. The sections were dewaxed and rehydrated, stained with hematoxylin and eosin (HE staining), differentiated with 1% hydrochloric acid in alcohol, and returned to blue with ammonia water. The sections were sealed after dehydration with alcohol gradient, and observed under an optical microscope at 200×. Image-pro plus image processing software was used to analyze the fat vacuolar area.

When the energy intake of an obese body exceeds the energy consumption, a large amount of lipid accumulates in adipose cells, leading to expansion of adipose tissues, i.e. enlargement of adipose cells and increase of the fat vacuolar area [33].

Figure 8:
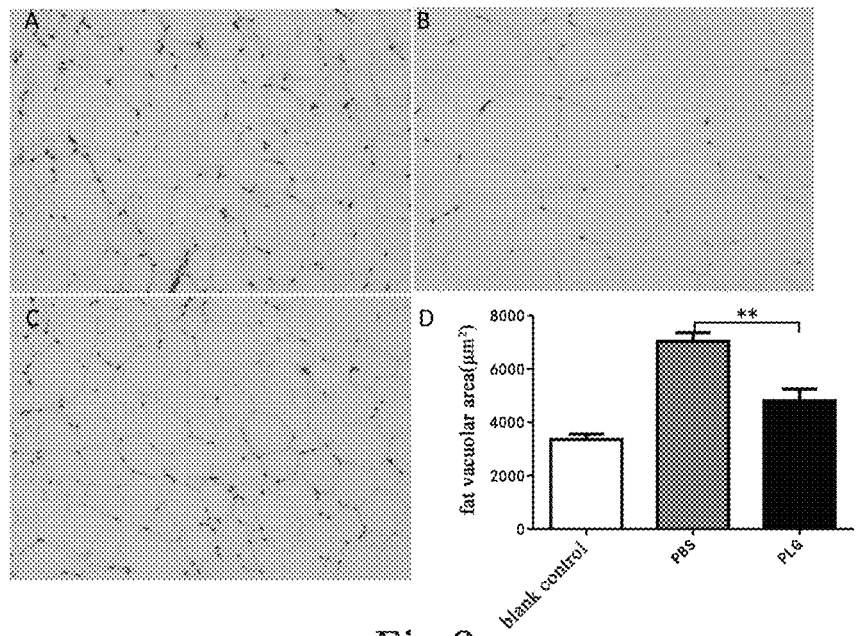
FIG. 8 shows statistical results of fat vacuolar area in abdominal fat by HE staining after administration of plasminogen to high-calorie diet-induced obesity model mice for 28 days. A represents the blank control group, B represents the control group administered with vehicle PBS, C represents the group administered with plasminogen, and D represents the quantitative analysis results. The results showed that the average fat vacuolar area in the group administered with plasminogen was remarkably less than that in the control group administered with vehicle PBS, and the statistical difference was extremely significant (** indicates P<0.01); and compared with the control group administered with vehicle PBS, the fat vacuolar area of mice in the group administered with plasminogen was closer to that in the blank control group. It indicates that plasminogen can significantly reduce the size of adipose cells and abdominal fat deposition of obesity model mice.

The results showed that the fat vacuolar area of mice in the group administered with plasminogen (FIG. 8C) was remarkably less than that in the control group administered with vehicle PBS (FIG. 8B), and the statistical difference was extremely significant (** indicates P<0.01) (FIG. 8D); and compared with the control group administered with vehicle PBS, the fat vacuolar area of mice in the group administered with plasminogen was closer to that in the blank control group (FIG. 8A). It indicates that plasminogen can significantly reduce the size of adipose cells and abdominal fat deposition of obesity model mice.

Example 2. Plasminogen Lowers the Concentration of Serum Leptin in Mice with Early-Stage Diabetes Mellitus Twelve 14- to 15-week-old male db/db mice and three db/m mice were taken. db/db mice were weighed and then randomly divided into two groups based on the body weight, 6 mice in each of the group administered with plasminogen and the control group administered with vehicle PBS. The first day of administration was recorded as the Day 1. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 28 consecutive days. As the normal control mice, db/m mice were not administered. On Day 28, the mice were fasted for 16 hours, and on Day 29, the blood was taken from removed eyeballs, and centrifuged to obtain a supernatant, which was detected for the concentration of serum leptin. The leptin level in the above-mentioned serum was detected using a serum leptin detection kit (Nanjing Jiancheng Bioengineering Institute, Cat #H174) according to the method of the detection kit.

Figure 9:
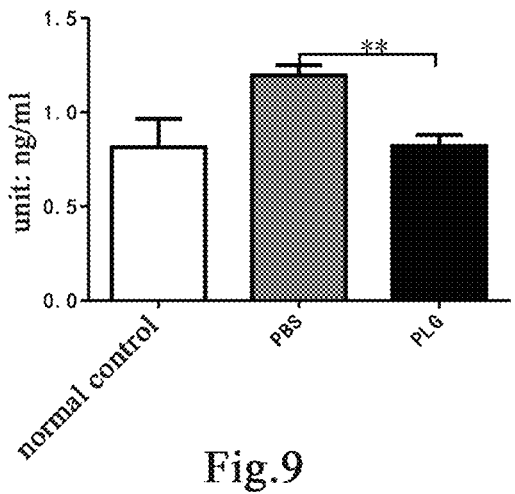
FIG. 9 shows detection results of serum leptin after administration of plasminogen to 14- to 15-week-old diabetic mice for 28 days. The results showed that the serum leptin concentration in mice in the group administered with plasminogen was remarkably lower than that in the control group administered with vehicle PBS, and the statistical difference was extremely significant (** indicates P<0.01); and compared with the control group administered with vehicle PBS, the serum leptin level of mice in the group administered with plasminogen was closer to that of normal mice. It indicates that plasminogen can reduce the serum leptin level in mice with early-stage type 2 diabetes mellitus.

The results showed that the serum leptin concentration in mice in the group administered with plasminogen was remarkably lower than that in the control group administered with vehicle PBS, and the statistical difference was significant (** indicates P<0.01); and compared with the control group administered with vehicle PBS, the serum leptin level of mice in the group administered with plasminogen was closer to that of normal mice (FIG. 9). It indicates that plasminogen can significantly reduce the serum leptin level in mice with early-stage type 2 diabetes mellitus.

Example 3. Plasminogen Lowers the Concentration of Serum Leptin in Mice with Late-Stage Diabetes Mellitus Thirteen 23- to 25-week-old male db/db mice were weighed and then randomly divided into two groups based on the body weight, 7 mice in the group administered with plasminogen, and 6 mice in the control group administered with vehicle PBS. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 28 consecutive days. On Day 28, the mice were fasted for 16 hours, and on Day 29, the blood was taken from removed eyeballs, and centrifuged to obtain a supernatant, which was detected for the concentration of serum leptin. The leptin level in the above-mentioned serum was detected using a serum leptin detection kit (Nanjing Jiancheng Bioengineering Institute, Cat #H174) according to the method of the detection kit.

Figure 10:
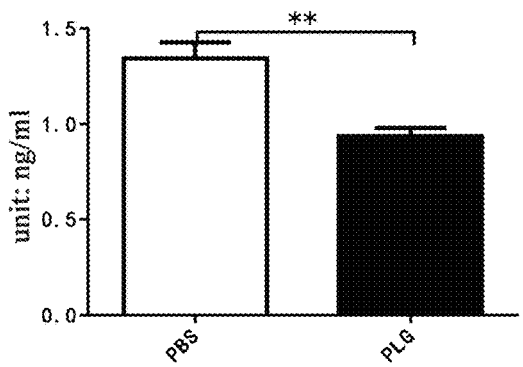
FIG. 10 shows detection results of serum leptin after administration of plasminogen to 23- to 25-week-old diabetic mice for 28 days. The results showed that the serum leptin concentration of mice in the group administered with plasminogen was remarkably lower than that in the control group administered with vehicle PBS, and the statistical difference was extremely significant (** indicates P<0.01). It indicates that plasminogen can reduce the serum leptin level in mice with late-stage type 2 diabetes mellitus.

The results showed that the serum leptin concentration of mice in the group administered with plasminogen was remarkably lower than that in the control group administered with vehicle PBS, and the statistical difference was extremely significant (** indicates P<0.01) (FIG. 10). It indicates that plasminogen can reduce the serum leptin level in mice with late-stage type 2 diabetes mellitus.

Example 4. Plasminogen Reduces the Fat Deposition in Liver of 16-Week Hyperlipemia Model Mice Eleven 6-week-old male C57 mice were fed with a high-fat and high-cholesterol diet (Nantong TROPHIC, TP2031) for 16 weeks to induce the hyperlipemia model [37, 38]. This model was designated as the 16-week hyperlipemia model. The model mice continued to be fed with a high-cholesterol diet. 50 µL of blood was taken from each mouse three days before administration, and the total cholesterol (T-CHO) content was detected. The mice were randomly divided into two groups based on the T-CHO content, 6 mice in the control group administered with vehicle PBS, and 5 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The livers were fixed in 4% paraformaldehyde for 24 to 48 hours, then sedimented in 15% and 30% sucrose at 4° C. overnight, respectively, and embedded in OCT. The frozen sections were 8 µm thick, stained with oil red O for 15 min, differentiated with 75% ethanol for 5 s, followed by nuclear staining with hematoxylin for 30 s, and sealing with glycerine and gelatin. The sections were observed under an optical microscope at 400×.

Figure 11:
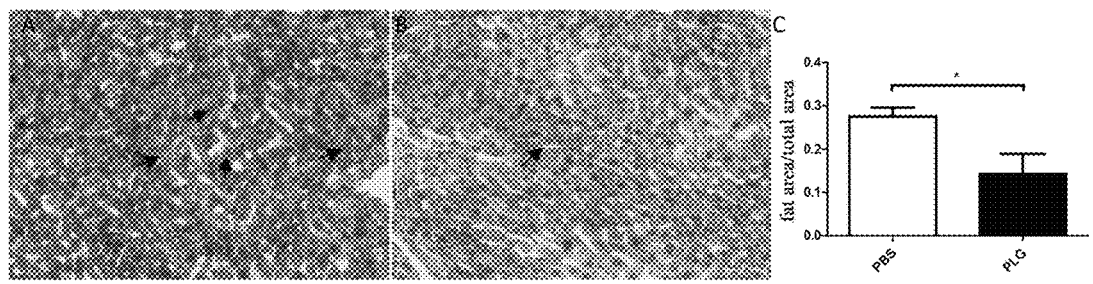
FIG. 11 shows observed results of oil red O staining of liver after administration of plasminogen to 16-week hyperlipemia model mice for 30 days. A represents the control group administered with vehicle PBS, B represents the group administered with plasminogen, and C represents the quantitative analysis results. The results showed that the fat deposition in liver of mice in the group administered with plasminogen was remarkably lower than that in the control group administered with vehicle PBS, and the quantitative analysis showed significant statistical difference (* indicates P<0.05). It indicates that plasminogen can ameliorate fat deposition in liver of hyperlipemia model mice.

Oil red O staining can show lipid deposition and reflect the extent of lipid deposition [39]. The results showed that the fat deposition in liver of mice in the group administered with plasminogen (FIG. 11B) was remarkably lower than that in the control group administered with vehicle PBS (FIG. 11A), and the quantitative analysis showed significant statistical difference (FIG. 11C). It indicates that plasminogen can reduce fat deposition in liver of hyperlipemia model mice.

Example 5. Plasminogen Reduces Lipid Deposition in Aortic Sinus of 16-Week Hyperlipemia Model Mice Eleven 6-week-old male C57 mice were fed with a high-fat and high-cholesterol diet (Nantong TROPHIC, TP2031) for 16 weeks to induce the hyperlipemia model [37, 38]. This model was designated as the 16-week hyperlipemia model. The model mice continued to be fed with a high-cholesterol diet. 50 µL of blood was taken from each mouse three days before administration, and the total cholesterol (T-CHO) content was detected. The mice were randomly divided into two groups based on the T-CHO content, 6 mice in the control group administered with vehicle PBS, and 5 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The heart tissues were fixed in 4% paraformaldehyde for 24 to 48 hours, then sedimented in 15% and 30% sucrose at 4° C. overnight, respectively, and embedded in OCT. The frozen sections of aortic sinus were 8 µm thick, stained with oil red O for 15 min, differentiated with 75% ethanol for 5 s, followed by nuclear staining with hematoxylin for 30 s, and sealing with glycerine and gelatin. The sections were observed under an optical microscope at 40× (FIGS. 11A and 11B) and 200× (FIGS. 11C and 11D).

Figure 12:
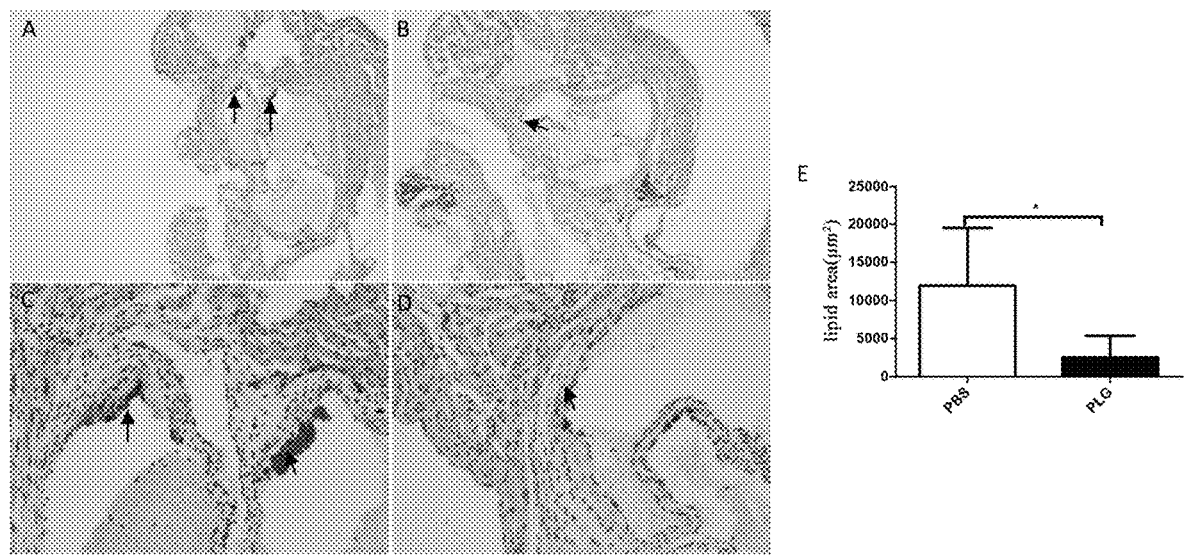
FIG. 12 shows observed results of oil red O staining of aortic sinus after administration of plasminogen to 16-week hyperlipemia model mice for 30 days. A and C represent the control group administered with vehicle PBS, B and D represent the group administered with plasminogen, and E represents the quantitative analysis results. The results showed that the fat deposition in aortic sinus of mice in the group administered with plasminogen was remarkably lower than that in the control group administered with vehicle PBS, and the statistical difference was significant (* indicates P<0.05). It indicates that plasminogen can ameliorate fat deposition in aortic sinus of hyperlipemia model mice.

The results showed that the fat deposition in aortic sinus of mice in the group administered with plasminogen (FIGS. 12B and 12D) was remarkably lower than that in the control group administered with vehicle PBS (FIGS. 12A and 12C), and the statistical difference was significant (FIG. 12E). It indicates that plasminogen can reduce lipid deposition in aortic sinus of hyperlipemia model mice.

Example 6. Plasminogen Lowers Fat Deposition in Kidney of 3% Cholesterol Diet-Induced Hyperlipemia Model Mice Sixteen 9-week-old male C57 mice were fed with a 3% cholesterol high-fat diet (Nantong TROPHIC) for 4 weeks to induce hyperlipemia [37-38]. This model was designated as the 3% cholesterol hyperlipemia model. The model mice continued to be fed with the 3% cholesterol high-fat diet. Another five male C57 mice of the same week age were taken as the blank control group, and were fed with a normal maintenance diet during the experiment. 50 µL of blood was taken from each mouse three days before administration, and the total cholesterol was detected. The model mice were randomly divided into two groups based on the total cholesterol concentration and the body weight, i.e., the group administered with plasminogen, and the control group administered with vehicle PBS, 8 mice in each group. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 30 days. The mice were sacrificed on Day 31. The kidneys were fixed in 4% paraformaldehyde for 24 to 48 hours, then sedimented in 15% and 30% sucrose at 4° C. overnight, respectively, and embedded in OCT. The frozen sections were 8 µm thick, stained with oil red O for 15 min, differentiated with 75% ethanol for 5 s, followed by nuclear staining with hematoxylin for 30 s, and sealing with glycerine and gelatin. The sections were observed under an optical microscope at 400×.

Figure 13:
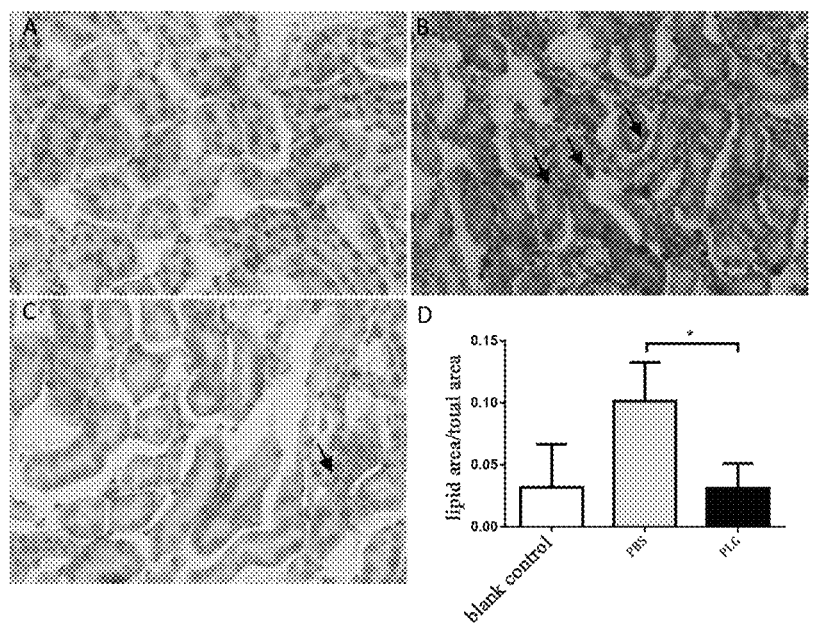
FIG. 13 shows observed results of oil red O of kidney after administration of plasminogen to 3% cholesterol diet-induced hyperlipemia model mice for 30 days. A represents the blank control group, B represents the control group administered with vehicle PBS, C represents the group administered with plasminogen, and D represents the quantitative analysis results. The results showed that the fat deposition in kidney (indicated by arrow) of mice in the group administered with plasminogen was remarkably less than that in the control group administered with vehicle PBS, and the quantitative analysis showed significant statistical difference; in addition, the lipid deposition level in the group administered with plasminogen was similar to that in mice in the blank control group. It indicates that plasminogen can reduce the fat deposition in kidney of hyperlipemia model mice, and thus reduce renal injury caused by fat deposition.

The results showed that the fat deposition in kidney (indicated by arrow) of mice in the group administered with plasminogen (FIG. 13C) was remarkably less than that in the control group administered with vehicle PBS (FIG. 13 B), and the quantitative analysis showed significant statistical difference (FIG. 13D); in addition, the lipid deposition level in the group administered with plasminogen was similar to that in mice in the blank control group (FIG. 13A). It indicates that plasminogen can reduce the fat deposition in kidney of 3% cholesterol hyperlipemia model mice, and thus reduce renal injury caused by fat deposition.

Example 7. Plasminogen Lowers the Serum Low-Density Lipoprotein Cholesterol Level in 3% Cholesterol Diet-Induced Hyperlipemia Model Mice Sixteen 9-week-old male C57 mice were fed with a 3% cholesterol high-fat diet (Nantong TROPHIC) for 4 weeks to induce hyperlipemia [37-38]. This model was designated as the 3% cholesterol hyperlipemia model. The model mice continued to be fed with a 3% cholesterol high-fat diet. 50 µL of blood was taken from each mouse three days before administration, and the total cholesterol was detected. The mice were randomly divided into two groups based on the total cholesterol concentration and the body weight, 8 mice in each group. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 20 days.

On Day 20, the mice fasted for 16 hours, and on Day 21, 50 µL of blood was collected from orbital venous plexus, and centrifuged to obtain a supernatant. The low-density lipoprotein cholesterol (LDL-C) was detected using a low-density lipoprotein cholesterol detection kit (Nanjing Jiancheng Bioengineering Institute, Cat #A113-1).

Figure 14:
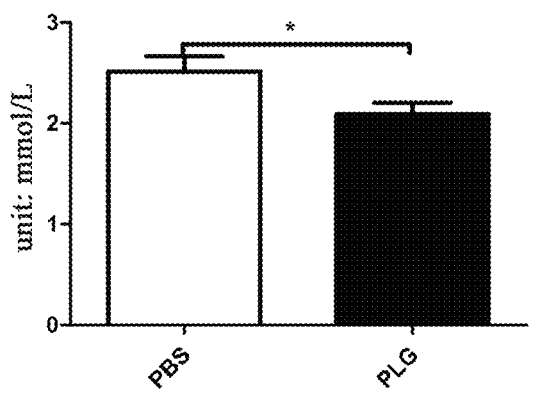
FIG. 14 shows detection results of serum low-density lipoprotein cholesterol after administration of plasminogen to 3% cholesterol diet-induced hyperlipemia model mice for 20 days. The results showed that the concentration of serum low-density lipoprotein cholesterol in mice in the group administered with plasminogen was remarkably lower than that in the control group administered with vehicle PBS, and the statistical difference was significant (* indicates P<0.05). It indicates that plasminogen can lower the content of low-density lipoprotein cholesterol in serum of hyperlipemia model mice, and has an effect of improving hyperlipemia.

The results showed that the concentration of LDL-C in mice in the group administered with plasminogen was remarkably lower than that in the control group administered with vehicle PBS, and the statistical difference was significant (FIG. 14). It indicates that plasminogen can lower the content of low-density lipoprotein cholesterol in serum of hyperlipemia model mice.

Example 8. Plasminogen Lowers Risk of Atherosclerosis Formation in 3% Cholesterol Diet-Induced Hyperlipemia Model Mice Sixteen 9-week-old male C57 mice were fed with a 3% cholesterol high-fat diet (Nantong TROPHIC) for 4 weeks to induce hyperlipemia [37-38]. This model was designated as the 3% cholesterol hyperlipemia model. The model mice continued to be fed with a 3% cholesterol high-fat diet. 50 µL of blood was taken from each mouse three days before administration, and the total cholesterol (T-CHO) was detected. The mice were randomly divided into two groups based on the total cholesterol concentration and the body weight, 8 mice in each group. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. After administration on Day 20, the mice began to fast for 16 hours, and on Day 21, 50 µL of blood was collected from orbital venous plexus, and centrifuged to obtain a supernatant. The total cholesterol content was detected by using a total cholesterol detection kit (Nanjing Jiancheng Bioengineering Institute, Cat #A111-1); and the high-density lipoprotein cholesterol (HDL-C) content was detected using a high-density lipoprotein cholesterol detection kit (Nanjing Jiancheng Bioengineering Institute, Cat #A112-1).

Atherosclerosis index is a comprehensive index to predict atherosclerosis clinically. It is considered to be of greater clinical importance as an estimate of the risk of coronary heart disease than total cholesterol, triglyceride, high-density lipoprotein, and low-density lipoprotein alone [40]. Atherosclerosis index=(T-CHO-HDL-C)/HDL-C.

Figure 15:
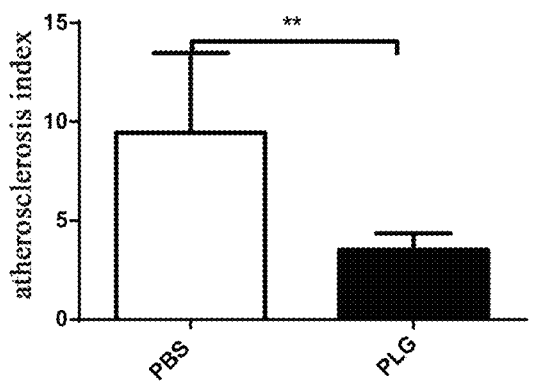
FIG. 15 shows detection results of serum atherosclerosis index after administration of plasminogen to 3% cholesterol diet-induced hyperlipemia model mice for 20 days. The results showed that the atherosclerosis index of mice in the group administered with plasminogen was remarkably lower than that in the control group administered with vehicle PBS, and the statistical difference was extremely significant (* * indicates P<0.01). It indicates that plasminogen can effectively lower the risk of atherosclerosis in hyperlipemia model mice.

The calculation results showed that the atherosclerosis index of mice in the group administered with plasminogen was remarkably lower than that in the control group administered with vehicle PBS, and the statistical difference was significant (FIG. 15). It indicates that plasminogen can lower the risk of atherosclerosis in hyperlipemia model mice.

Example 9. Plasminogen Lowers the Content of Serum Total Cholesterol in ApoE Atherosclerosis Mice Thirteen 6-week-old male ApoE mice were fed with a high-fat and high-cholesterol diet (Nantong TROPHIC, TP2031) for 16 weeks to induce the atherosclerosis model [41-42] The model mice continued to be fed with a high-fat and high-cholesterol diet. 50 µL of blood was taken from each mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 30 days. On Day 30, the mice fasted for 16 hours, and on Day 31, the blood was collected from removed eyeballs, and centrifuged to obtain a supernatant, which was detected for the total cholesterol using a total cholesterol detection kit (Nanjing Jiancheng Bioengineering Institute, Cat #A111-1).

Figure 16:
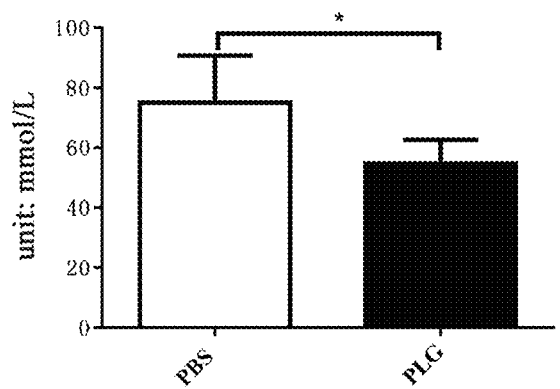
FIG. 16 shows detection results of serum total cholesterol after administration of plasminogen to ApoE atherosclerosis model mice for 30 days. The results showed that the concentration of total cholesterol in mice in the group administered with plasminogen was remarkably lower than that in the control group administered with vehicle PBS, and the statistical difference was significant (* indicates P<0.05). It indicates that plasminogen can lower the content of total cholesterol in serum of ApoE atherosclerosis model mice, and improve the dyslipidemia in atherosclerosis model mice.

The detection results showed that the concentration of total cholesterol in mice in the group administered with plasminogen was remarkably lower than that in the control group administered with vehicle PBS, and the statistical difference was significant (P=0.014) (FIG. 16). It indicates that plasminogen can lower the content of total cholesterol in serum of ApoE atherosclerosis model mice, and improve the dyslipidemia of atherosclerosis.

Example 10. Plasminogen Lowers the Content of Serum Triglyceride in ApoE Atherosclerosis Mice Thirteen 6-week-old male ApoE mice were fed with a high-fat and high-cholesterol diet (Nantong TROPHIC, TP2031) for 16 weeks to induce the atherosclerosis model [41-42] The model mice continued to be fed with a high-fat and high-cholesterol diet. 50 µL of blood was taken from each mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 30 days. On Day 30, the mice fasted for 16 hours, and on Day 31, the blood was collected from removed eyeballs, and centrifuged to obtain a supernatant, which was detected for triglyceride using a triglyceride detection kit (Nanjing Jiancheng Bioengineering Institute, Cat #A110-1).

Figure 17:
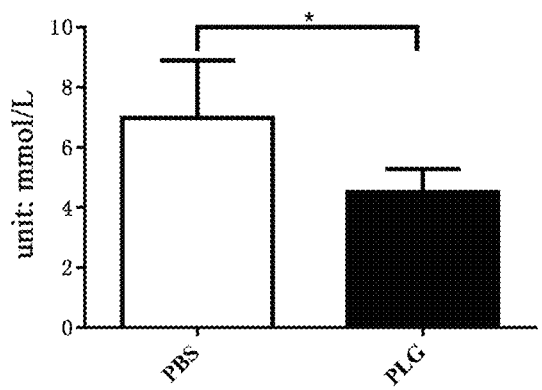
FIG. 17 shows detection results of serum triglyceride after administration of plasminogen to ApoE atherosclerosis model mice for 30 days. The results showed that the concentration of triglyceride in mice in the group administered with plasminogen was remarkably lower than that in the control group administered with vehicle PBS, and the statistical difference was significant (* indicates P<0.05). It indicates that plasminogen can lower the content of triglyceride in serum of ApoE atherosclerosis model mice, and improve the dyslipidemia in atherosclerosis model mice.

The detection results showed that the concentration of triglyceride in mice in the group administered with plasminogen was remarkably lower than that in the control group administered with vehicle PBS, and the statistical difference was significant (P=0.013) (FIG. 17). It indicates that plasminogen can lower the content of triglyceride in serum of ApoE atherosclerosis model mice, and improve the dyslipidemia of atherosclerosis.

Example 11. Plasminogen Lowers the Content of Serum Low-Density Lipoprotein Cholesterol in ApoE Atherosclerosis Mice Thirteen 6-week-old male ApoE mice were fed with a high-fat and high-cholesterol diet (Nantong TROPHIC, TP2031) for 16 weeks to induce the atherosclerosis model [41-42] The model mice continued to be fed with a high-fat and high-cholesterol diet. 50 µL of blood was taken from each mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 30 days. On Day 30, the mice fasted for 16 hours, and on Day 31, the blood was collected from removed eyeballs, and centrifuged to obtain a supernatant, which was detected for LDL-C using a low-density lipoprotein cholesterol (LDL-C) detection kit (Nanjing Jiancheng Bioengineering Institute, Cat #A113-1).

Figure 18:
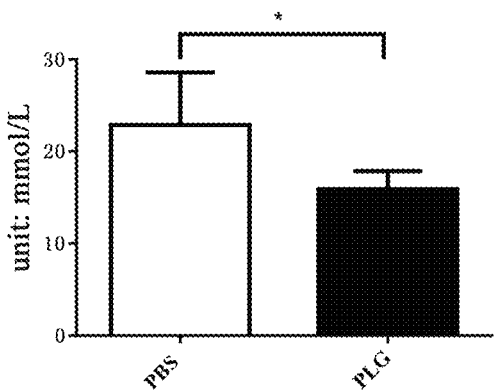
FIG. 18 shows detection results of serum low-density lipoprotein cholesterol after administration of plasminogen to ApoE atherosclerosis model mice for 30 days. The results showed that the concentration of serum low-density lipoprotein cholesterol in mice in the group administered with plasminogen was remarkably lower than that in the control group administered with vehicle PBS, and the statistical difference was significant (* indicates P<0.05). It indicates that plasminogen can lower the content of low-density lipoprotein cholesterol in serum of ApoE atherosclerosis model mice, and improve the dyslipidemia in atherosclerosis model mice.

The results showed that the concentration of LDL-C in mice in the group administered with plasminogen was remarkably lower than that in the control group administered with vehicle PBS, and the statistical difference was significant (P=0.017) (FIG. 18). It indicates that plasminogen can lower the content of low-density lipoprotein cholesterol in serum of ApoE atherosclerosis model mice, and improve the dyslipidemia in atherosclerosis model mice.

Example 12. Plasminogen Improves Expression of Hypothalamic Leptin Receptor in Obesity Model Mice Fourteen 8-week-old male C57 mice were randomly divided into two groups based on the body weight, a blank control group of 4 mice and a model group of 10 mice. Mice in the blank control group were fed with a normal maintenance diet; mice in the model group were fed with a high-fat diet containing 45% fat calories (TP23000, Nantong TROPHIC Feed Technology Co., Ltd.) for model establishment for 12 weeks to establish an obesity model [1]. After 12 weeks, mice in the model group were weighed and randomly divided into two groups again based on the body weight, 5 mice in each of a group administered with plasminogen and a control group administered with vehicle PBS. The mice in the group administered with plasminogen were injected with human plasminogen at a dose of 1 mg/0.1 mL/mouse/day via the tail vein, and the mice in the control group administered with vehicle PBS were injected with an equal volume of PBS via the tail vein, both lasting for 28 consecutive days. The blank control group was not injected with any liquid. During the administration, mice continued to be fed with a model establishment diet. The mice were sacrificed on Day 29. The hypothalami were fixed in 4% paraformaldehyde for 24 to 48 hours. The fixed tissues were paraffin-embedded after dehydration with alcohol gradient and permeabilization with xylene. The thickness of the tissue sections was 4 μm. The sections were dewaxed and rehydrated and washed with water once. The sections were repaired with citric acid for 30 minutes, and gently rinsed with water after cooling at room temperature for 10 minutes. The sections were incubated with 3% hydrogen peroxide for 15 minutes, and the tissues were circled with a PAP pen. The sections were blocked with 10% goat serum (Vector laboratories, Inc., USA) for 1 hour, and after the time was up, the goat serum liquid was discarded. The sections were incubated with anti-leptin receptor antibody (Abcam) overnight at 4□ and washed with PBS twice for 5 minutes each time. The sections were incubated with a secondary antibody, goat anti-rabbit IgG (HRP) antibody (Abcam), for 1 hour at room temperature and washed with PBS twice for 5 minutes each time. The sections were developed with a DAB kit (Vector laboratories, Inc., USA). After washing with water three times, the sections were counterstained with hematoxylin for 30 seconds, returned to blue with running water for 5 minutes, and washed with PBS once. After dehydration with a gradient, permeabilization and sealing, the sections were observed under an optical microscope at 40× (Figures A-C) and 200× (Figures E and F).

The leptin receptor has a main physiological function of binding with leptin, facilitates the physiological role of leptin in regulating energy balance, fat storage, reproductive activities and the like in the body, and also participates in the autocrine regulation of leptin. Different types of leptin receptors are selectively expressed in central and peripheral tissues [45-47].

Figure 19:
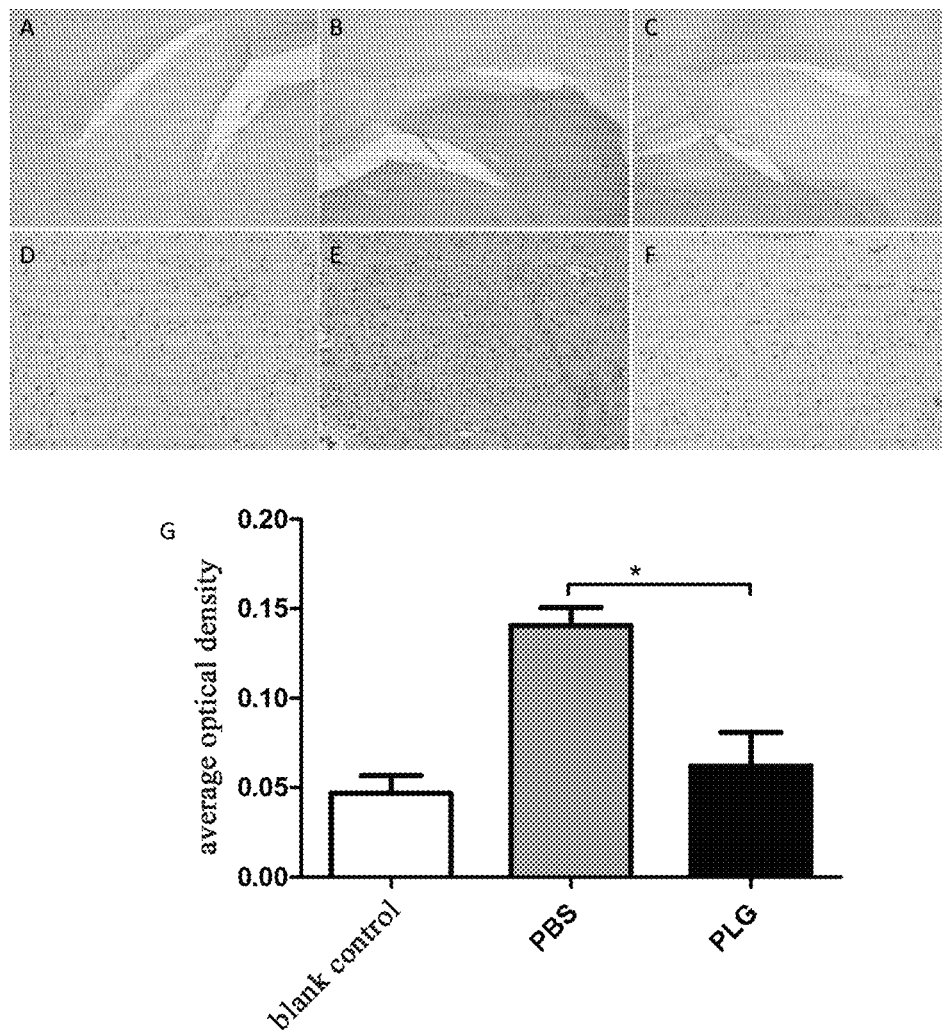
FIG. 19 shows immunohistochemical staining results of hypothalamic leptin receptor after administration of plasminogen to obesity model mice. A and D represent the blank control group, B and E represent the control group administered with vehicle PBS, C and F represent the group administered with plasminogen, and G represents the quantitative analysis results. The results showed that the expression of hypothalamic leptin receptor in mice in the control group administered with vehicle PBS was remarkably greater than that in the blank control group; while the expression of hypothalamic leptin receptor in mice in the group administered with plasminogen was remarkably less than that in the control group administered with vehicle PBS, and was close to the blank control group in the expression level, and the statistical difference was significant (P=0.01). It indicates that plasminogen can significantly reduce expression of hypothalamic leptin receptor in obese mice.

The results showed that the expression of hypothalamic leptin receptor in mice in the control group administered with vehicle PBS (FIGS. 19B and E) was remarkably greater than that in the blank control group (FIGS. 19A and D); while the expression of hypothalamic leptin receptor in mice in the group administered with plasminogen (FIGS. 19C and F) was remarkably less than that in the control group administered with vehicle PBS, and was close to the blank control group in the expression level, and the statistical difference was significant (P=0.01) (FIG. 19G). It indicates that plasminogen can significantly reduce expression of hypothalamic leptin receptor in obese mice.

REFERENCES

[1] http://www.ama-assn.org/ama/pub/news/news/2013/2013-06-18-new-ama-policies-annual-meeting [EB/OL] (2013-06-18).page.
[2] http://www.who.int/mediacentre/factsheets/fs311/en/ [EB/OL](2015-01-26).
[3] HOU X, LU J, WENG J, et al. Impact of waist circumference and body mass index on risk of cardiometabolic disorder and cardiovascular disease in Chinese adults: a national diabetes and metabolic disorders survey [J]. PLoS One, 2013, 8 (3):e57319.
[4] LI S, XIAO J, JI L, et al. BMI and waist circumference are associated with impaired glucose metabolism and type 2 diabetes in normal weight Chinese adults [J]. J Diabet Complicat, 2014, 28(4): 470-476.
[5] Christensen R, Kristensen P K, et al. Efficacy and safety of the weightloss drug rimonabant: a meta-analysis of randomised trials [J]. Lancet, 2007, 370(9600):1706-1713.
[6] James W P, Caterson I D, et al. Effect of sibutramine on cardiovascular outcomes in overweight and obese subjects [J]. N Engl J Med, 2010, 363(10):905-917.
[7] Kopelmanl P, Groot Gde H, et al. Weight Loss, HbA1c Reduction, and Tolerability of Cetilistat in a Randomized, Placebo-controlled Phase 2 Trial in Obese Diabetics: Comparison With Orlistat (Xenical) [J]. Obesity, 2010, 18(1): 108-115.
[8] APOVIAN C M, A R ONNE L J, BESSESEN D H, et al. Pharmacological management of obesity: an endocrine Society clinical practice guideline [J]. J Clin Endocrinol Metab, 2015, 100 (2):342-362.
[9] Alexander C M and Werb, Z. (1991). Extracellular matrix degradation. In Cell Biology of Extracellular Matrix, Hay E D, ed. (New York: Plenum Press), pp. 255-302.
[10] Werb, Z., Mainardi, C. L., Vater, C. A., and Harris, E. D., Jr. (1977). Endogenous activation of latent collagenase by rheumatoid synovial cells. Evidence for a role of plasminogen activator. N. Engl. J. Med. 296, 1017-1023.
[11] He, C. S., Wilhelm, S. M., Pentland, A. P., Manner, B. L., Grant, G A., Eisen, A. Z., and Goldberg, G I. (1989).

Tissue cooperation in a proteolytic cascade activating human interstitial collagenase. Proc. Natl. Acad. Sci. U.S.A 86, 2632-2636.

[12] Stoppelli, M. P., Corti, A., Soffientini, A., Cassani, G, Blasi, F., and Assoian, R. K. (1985). Differentiation-enhanced binding of the amino-terminal fragment of human urokinase plasminogen activator to a specific receptor on U937 monocytes. Proc. Natl. Acad. Sci. U.S.A 82, 4939-4943.

[13] Vassalli, J. D., Baccino, D., and Belin, D. (1985). A cellular binding site for the Mr 55,000 form of the human plasminogen activator, urokinase. J. Cell Biol. 100, 86-92.

[14] Wiman, B. and Wallen, P. (1975). Structural relationship between "glutamic acid" and "lysine" forms of human plasminogen and their interaction with the NH2-terminal activation peptide as studied by affinity chromatography. Eur. J. Biochem. 50, 489-494.

[15] Saksela, O. and Rifkin, D. B. (1988). Cell-associated plasminogen activation: regulation and physiological functions. Annu. Rev. Cell Biol. 4, 93-126.

[16] Raum, D., Marcus, D., Alper, C. A., Levey, R., Taylor, P. D., and Starzl, T. E. (1980). Synthesis of human plasminogen by the liver. Science 208, 1036-1037.

[17] Wallén P (1980). Biochemistry of plasminogen. In Fibrinolysis, Kline D L and Reddy K K N, eds. (Florida: CRC)

[18] Sottrup-Jensen, L., Zajdel, M., Claeys, H., Petersen, T. E., and Magnusson, S. (1975). Amino-acid sequence of activation cleavage site in plasminogen: homology with "pro" part of prothrombin. Proc. Natl. Acad. Sci. U.S.A 72, 2577-2581.

[19] Collen, D. and Lijnen, H. R. (1991). Basic and clinical aspects of fibrinolysis and thrombolysis. Blood 78, 3114-3124.

[20] Alexander, C. M. and Werb, Z. (1989). Proteinases and extracellular matrix remodeling. Curr. Opin. Cell Biol. 1, 974-982.

[21] Mignatti, P. and Rifkin, D. B. (1993). Biology and biochemistry of proteinases in tumor invasion. Physiol Rev. 73, 161-195.

[22] Collen, D. (2001). Ham-Wasserman lecture: role of the plasminogen system in fibrin-homeostasis and tissue remodeling. Hematology. (Am. Soc. Hematol. Educ. Program) 1-9.

[23] Rifkin, D. B., Moscatelli, D., Bizik, J., Quarto, N., Blei, F., Dennis, P., Flaumenhaft, R., and Mignatti, P. (1990). Growth factor control of extracellular proteolysis. Cell Differ. Dev. 32, 313-318.

[24] Andreasen, P. A., Kjoller, L., Christensen, L., and Duffy, M. J. (1997). The urokinase-type plasminogen activator system in cancer metastasis: a review. Int. J. Cancer 72, 1-22.

[25] Rifkin, D. B., Mazzieri, R., Munger, J. S., Noguera, I., and Sung, J. (1999). Proteolytic control of growth factor availability. APMIS 107, 80-85.

[26] Marder V J, Novokhatny V. Direct fibrinolytic agents: biochemical attributes, preclinical foundation and clinical potential [J]. Journal of Thrombosis and Haemostasis, 2010, 8(3): 433-444.

[27] Hunt J A, Petteway Jr S R, Scuderi P, et al. Simplified recombinant plasmin: production and fu-nctional comparison of a novel thrombolytic molecule with plasma-derived plasmin [J]. Thromb Haemost, 2008, 100(3): 413-419.

[28] Sottrup-Jensen L, Claeys H, Zajdel M, et al. The primary structure of human plasminogen: Isolation of two lysine-binding fragments and one "mini"-plasminogen (MW, 38,000) by elastase-catalyzed-specific limited proteolysis [J]. Progress in chemical fibrinolysis and thrombolysis, 1978, 3: 191-209.

[29] Nagai N, Demarsin E, Van Hoef B, et al. Recombinant human microplasmin: production and potential therapeutic properties [J]. Journal of Thrombosis and Haemostasis, 2003, 1(2): 307-313.

[30] Eun Young Lee, Yeon Wook Kim, Anti-obesity effects of KR-66195, a synthetic DPP-IV inhibitor, in diet-induced obese mice and obese-diabetic ob/ob mice, Metabolism clinical and experimental 63 (2014) 793-799

[31] Yang Z, Li W, He C. Potential effect of chronic *Helicobacter pylori* infection on glucose metabolism of Mongolian gerbils. World J Gastroenterol. 2015 Nov. 28; 21(44):12593-604.

[32] Hu Y, Rosa G J, Gianola D. A GWAS assessment of the contribution of genomic imprinting to the variation of body mass index in mice. BMC Genomics. 2015 Aug. 5; 16:576.

[33] Goossens G H. The role of adipose tissue dysfunction in the pathogenesis of obesity-related insulin resistance. Physiol Behav. 2008 May 23; 94(2):206-18.

[34] Sahu A. Leptin signaling in the hypothalamus: emphasis on energy homeostasis and leptin resistance. Front Neuroendocrinol. 2003 Dec.; 24(4):225-53.

[35] Harris R B, Mitchell T D, Yan X et al. Metabolic responses to leptin in obese db/db mice are strain dependent. Am J Physiol Regul Integr Comp Physiol. 2001 July; 281(1):R115-32.

[36] Ennequin Gl, Boisseau Nl, Caillaud K et al. Neuregulin 1 affects leptin levels, food intake and weight gain in normal-weight, but not obese, db/db mice. Diabetes Metab. 2015 April; 41(2):168-72.

[37] Dominika Nackiewicz, Paromita Dey, Barbara Szczerba et al Inhibitor of differentiation 3, a transcription factor regulates hyperlipidemia associated kidney disease. Nephron Exp Nephrol. 2014; 126(3): 141-147.

[38] Ming Gul, Yu Zhang., Shengjie Fan et al. Extracts of Rhizoma Polygonati Odorati Prevent High-Fat Diet-Induced Metabolic Disorders in C57BL/6 Mice. PLoS ONE 8(11): e81724.

[39] Siobhan M. Craige, PhD, Shashi Kant et al. Endothelial NADPH oxidase 4 protects ApoE−/− mice from atherosclerotic lesions. Free Radic Biol Med. 2015 December; 89: 1-7.

[40] Sungwon Lee, Youngjoo Lee, Jiyeon Kim et al. Atorvastatin and rosuvastatin improve physiological parameters and alleviate immune dysfunction in metabolic disorders. Biochem Biophys Res Commun. 2016 Sep. 23; 478(3):1242-7.

[41] Yutaka Nakashima, Andrew S. Plump, Elaine W. Raines et al. Arterioscler Thromb. 1994 January; 14(1):133-40.

[42] Yvonne Nitschke, Gabriele Weissen-Plenz, Robert Terkeltaub et al. Nppl promotes atherosclerosis in ApoE knockout mice. J. Cell. Mol. Med. Vol 15, No 11, 2011 pp. 2273-2283.

[43] Duan D M, Wu S, Hsu L A et al. Associations between TRPV4 genotypes and body mass index in Taiwanese subjects. Mol Genet Genomics. 2015 August; 290(4): 1357-65.

[44] Goossens G H. The role of adipose tissue dysfunction in the pathogenesis of obesity-related insulin resistance. Physiol Behav. 2008 May 23; 94(2):206-18.

[45] Shimizu H1, Shimomura K, Negishi M et al. Circulating concentrations of soluble leptin receptor: influence of menstrual cycle and diet therapy. Nutrition. 2002 April; 18(4): 309-12.

[46] Kastin A Jl, Pan W, Maness L M et al. Decreased transport of leptin across the blood-brain barrier in rats lacking the short form of the leptin receptor. Peptides. 1999 December; 20(12):1449-53.

[47] Münzberg Hl, Flier J S, Bjørbaek C. Region-specific leptin resistance within the hypothalamus of diet-induced obese mice. Endocrinology. 2004 November; 145(11): 4880-9. Epub 2004 Jul. 22.

The invention claimed is:

1. A method for treating obesity in a subject, comprising administering an effective amount of plasminogen to the subject.

2. The method of claim 1, wherein the method reduces abnormal or excessive lipid deposition in a subcutis, a heart, a liver, lungs, kidneys, blood vessels, a mesentery, a peritoneum, or a body cavity, or around an organ.

3. The method of claim 1, wherein the method lowers a level of blood lipid in the subject.

4. The method of claim 3, wherein the blood lipid is triglyceride or low-density lipoprotein.

5. The method of claim 1, wherein the obesity is simple obesity or obesity secondary to a disease or condition selected from the group consisting of an endocrine disorder disease, a glucose metabolism disease, a liver disease, a kidney disease, a cardiovascular disease, an intestinal disease, a thyroid disease, a gallbladder or biliary tract disease, and excessive drinking.

6. The method of claim 1, wherein the obesity comprises obesity complicated with diabetes mellitus, obesity complicated with hypertension, obesity complicated with atherosclerosis, obesity complicated with a liver disease, or obesity complicated with osteoporosis.

7. The method of claim 1, wherein the method reduces abnormal or excessive fat deposition in the subject in one or more ways selected from:
   1) reducing abnormal or excessive lipid deposition in one or more sites selected from: a subcutis, a heart, a liver, lungs, kidneys, blood vessels, a mesentery, a peritoneum, and a body cavity, and around an organ,
   2) promoting clearance of hepatic fat, and
   3) promoting clearance of lipid in blood to reduce the onset risk of heart disease in the subject.

8. The method of claim 1, wherein the plasminogen is administered in combination with one or more other drugs.

9. The method of claim 1, wherein the plasminogen has at least 90% sequence identity with SEQ ID No. 2, and still has the plasminogen activity of proteolysis.

10. The method of claim 1, wherein the plasminogen is a protein that comprises a plasminogen active fragment of SEQ ID No. 14, and still has the plasminogen activity of proteolysis.

11. The method of claim 1, wherein the plasminogen is selected from Glu-plasminogen, Lys-plasminogen, mini-plasminogen, micro-plasminogen, and delta-plasminogen.

12. The method of claim 1, wherein the plasminogen is a natural or synthetic human plasminogen.

13. The method of claim 1, wherein the method reduces weight in the subject.

14. The method of claim 13, wherein the subject is human.

15. The method of claim 1, wherein the plasminogen is administered to the subject at a dosage of 1-100 mg/kg at a frequency of weekly to daily.

16. The method of claim 15, wherein the plasminogen is administered at least daily.

* * * * *

SEQUENCE LISTING

<160> NUMBER OF SEQ ID NOS: 14

<210> SEQ ID NO 1
<211> LENGTH: 2376
<212> TYPE: DNA
<213> ORGANISM: Artificial sequence
<220> FEATURE:
<223> OTHER INFORMATION: nucleotide sequence coding for the natural
      plasminogen (Glu-PLG,Glu-plasminogen)without the signal peptide

<400> SEQUENCE: 1

```
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt tatttgaaaa gaaagtgtat     240
ctctcagagt gcaagactgg aatggaaag aactacagag ggacgatgtc caaaacaaaa     300
aatggcatca cctgtcaaaa atggagttcc acttctcccc acagacctag attctcacct     360
gctacacacc cctcagaggg actggaggag aactactgca ggaatccaga caacgatccg     420 cagggccct ggtgctatac tactgatcca gaaaagagat atgactactg cgacattctt     480
gagtgtgaag aggaatgtat gcattgcagt ggagaaaact atgacggcaa aatttccaag     540
accatgtctg actggaatg ccaggcctgg gactctcaga gcccacacgc tcatggatac     600
attccttcca aatttccaaa caagaacctg aagaagaatt actgtcgtaa ccccgatagg     660
gagctgcggc cttggtgttt caccaccgac cccaacaagc gctgggaact tgtgacatc     720 ccccgctgca caacacctcc accatcttct ggtcccacct accagtgtct gaagggaaca     780
ggtgaaaact atcgcgggaa tgtggctgtt accgtgtccg gcacacctg tcagcactgg     840 agtgcacaga cccctcacac acataacagg accagaaaa acttcccctg caaaaatttg     900
gatgaaaact actgccgcaa tcctgacgga aaagggccc catggtgcca tacaaccaac     960
agccaagtgc ggtgggagta ctgtaagata ccgtcctgtg actcctcccc agtatccacg    1020
gaacaattgg ctcccacagc accacctgag ctaaccctg tggtccagga ctgctaccat    1080
ggtgatggac agagctaccg aggcacatcc tccaccacca cacaggaaa gaagtgtcag    1140 tcttggtcat ctatgacacc acaccggcac cagaagaccc cagaaaacta cccaaatgct    1200
ggcctgacaa tgaactactg caggaatcca gatgccgata aaggcccctg gtgttttacc    1260
acagacccca cgtcaggtg ggagtactgc aacctgaaaa aatgctcagg aacagaagcg    1320
agtgttgtag cacctccgcc tgttgtcctg cttccagatg tagagactcc ttccgaagaa    1380
gactgtatgt ttgggaatgg aaaggatac cgaggcaaga gggcgaccac tgttactggg    1440
acgccatgcc aggactgggc tgcccaggag ccccatagac acagcatttt cactccagag    1500
acaaatccac gggcgggtct ggaaaaaaat tactgccgta accctgatgg tgatgtaggt    1560 ggtcctggt gctacgac aaatccaaga aaactttacg actactgtga tgtccctcag    1620
tgtgcggccc cttcatttga ttgtgggaag cctcaagtgg agccgaagaa atgtcctgga    1680
agggttgtag gggtgtgt ggcccaccca cattcctggc cctggcaagt cagtcttaga    1740
acaaggtttg gaatgcactt ctgtggaggc acccttgatat ccccagagtg ggtgttgact    1800
```

-continued

```
gctgcccact gcttggagaa gtccccaagg ccttcatcct acaaggtcat cctgggtgca      1860
caccaagaag tgaatctcga accgcatgtt caggaaatag aagtgtctag gctgttcttg      1920
gagcccacac gaaaagatat tgccttgcta agctaagca gtcctgccgt catcactgac       1980
aaagtaatcc cagcttgtct gccatcccca aattatgtgg tcgctgaccg gaccgaatgt      2040
ttcatcactg gctggggaga aacccaaggt acttttggag ctggccttct caaggaagcc     2100
cagctccctg tgattgagaa taaagtgtgc aatcgctatg agtttctgaa tggaagagtc      2160
caatccaccg aactctgtgc tgggcatttg gccggaggca ctgacagttg ccagggtgac     2220
agtggaggtc ctctggtttg cttcgagaag gacaaataca ttttacaagg agtcactcct     2280
tggggtcttg gctgtgcacg ccccaataag cctggtgtct atgttcgtgt ttcaaggttt      2340
gttacttgga ttgagggagt gatgagaaat aattaa                                 2376
```

<210> SEQ ID NO 2
<211> LENGTH: 791
<212> TYPE: PRT
<213> ORGANISM: Artificial sequence
<220> FEATURE:
<223> OTHER INFORMATION: amino acid sequence of the natural plasminogen
      (Glu-PLG,Glu-plasminogen) without the signal peptide

<400> SEQUENCE: 2

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Pro Ser Ser Gly Pro Thr Tyr Gln Cys
                245                 250                 255
```

-continued

```
Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
        275                 280                 285

Asn Arg Thr Pro Glu Asn Phe Pro Cys Lys Asn Leu Asp Glu Asn Tyr
    290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
        355                 360                 365

Thr Ser Ser Thr Thr Thr Thr Gly Lys Lys Cys Gln Ser Trp Ser Ser
    370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
                405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Pro Val
        435                 440                 445

Val Leu Leu Pro Asp Val Glu Thr Pro Ser Glu Glu Asp Cys Met Phe
    450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
                485                 490                 495

Phe Thr Pro Glu Thr Asn Pro Arg Ala Gly Leu Glu Lys Asn Tyr Cys
            500                 505                 510

Arg Asn Pro Asp Gly Asp Val Gly Gly Pro Trp Cys Tyr Thr Thr Asn
        515                 520                 525

Pro Arg Lys Leu Tyr Asp Tyr Cys Asp Val Pro Gln Cys Ala Ala Pro
    530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
                565                 570                 575

Val Ser Leu Arg Thr Arg Phe Gly Met His Phe Cys Gly Gly Thr Leu
            580                 585                 590

Ile Ser Pro Glu Trp Val Leu Thr Ala Ala His Cys Leu Glu Lys Ser
        595                 600                 605

Pro Arg Pro Ser Ser Tyr Lys Val Ile Leu Gly Ala His Gln Glu Val
    610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
                645                 650                 655

Val Ile Thr Asp Lys Val Ile Pro Ala Cys Leu Pro Ser Pro Asn Tyr
            660                 665                 670

Val Val Ala Asp Arg Thr Glu Cys Phe Ile Thr Gly Trp Gly Glu Thr
```

```
                     675                 680                 685
Gln Gly Thr Phe Gly Ala Gly Leu Leu Lys Glu Ala Gln Leu Pro Val
            690                 695                 700
Ile Glu Asn Lys Val Cys Asn Arg Tyr Glu Phe Leu Asn Gly Arg Val
705                 710                 715                 720
Gln Ser Thr Glu Leu Cys Ala Gly His Leu Ala Gly Gly Thr Asp Ser
                725                 730                 735
Cys Gln Gly Asp Ser Gly Gly Pro Leu Val Cys Phe Glu Lys Asp Lys
            740                 745                 750
Tyr Ile Leu Gln Gly Val Thr Ser Trp Gly Leu Gly Cys Ala Arg Pro
            755                 760                 765
Asn Lys Pro Gly Val Tyr Val Arg Val Ser Arg Phe Val Thr Trp Ile
        770                 775                 780
Glu Gly Val Met Arg Asn Asn
785                 790

<210> SEQ ID NO 3
<211> LENGTH: 2433
<212> TYPE: DNA
<213> ORGANISM: Artificial sequence
<220> FEATURE:
<223> OTHER INFORMATION: nucleotide sequence coding for the natural
      plasminogen (from swiss prot)with the signal peptide

<400> SEQUENCE: 3
atggaacata aggaagtggt tcttctactt cttttatttc tgaaatcagg tcaaggagag      60
cctctggatg actatgtgaa tacccagggg gcttcactgt tcagtgtcac taagaagcag     120
ctgggagcag aagtataga agaatgtgca gcaaaatgtg aggaggacga agaattcacc      180
tgcagggcat tccaatatca cagtaaagag caacaatgtg tgataatggc tgaaaacagg     240
aagtcctcca taatcattag gatgagagat gtagttttat ttgaaaagaa agtgtatctc     300
tcagagtgca agactgggaa tggaaagaac tacagaggga cgatgtccaa aacaaaaaat     360
ggcatcacct gtcaaaaatg gagttccact tctccccaca gacctagatt ctcacctgct     420
acacacccct cagagggact ggaggagaac tactgcagga atccagacaa cgatccgcag     480
gggccctggt gctatactac tgatccagaa aagagatatg actactgcga cattcttgag     540
tgtgaagagg aatgtatgca ttgcagtgga gaaaactatg acggcaaaat ttccaagacc     600
atgtctggac tggaatgcca ggcctgggac tctcagagcc cacacgctca tggatacatt     660
ccttccaaat ttccaaacaa gaacctgaag aagaattact gtcgtaaccc cgataggggag    720 ctgcggcctt ggtgtttcac caccgacccc aacaagcgct gggaactttg tgacatcccc     780
cgctgcacaa cacctccacc atcttctggt cccacctacc agtgtctgaa gggaacaggt     840
gaaaactatc gcgggaatgt ggctgttacc gtgtccgggc acacctgtca gcactggagt     900
gcacagaccc ctcacacaca taacaggaca ccagaaaaact ccccctgcaa aaatttggat    960
gaaaactact gccgcaatcc tgacggaaaa agggccccat ggtgccatac aaccaacagc    1020
caagtgcggt gggagtactg taagataccg tcctgtgact cctccccagt atccacggaa    1080
caattggctc ccacagcacc acctgagcta accctgtgg tccaggactg ctaccatggt     1140
gatggacaga gctaccgagg cacatcctcc accaccacca caggaaagaa gtgtcagtct    1200
tggtcatcta tgacaccaca ccggcaccag aagaccccag aaaactaccc aaatgctggc    1260
ctgacaatga actactgcag gaatccagat gccgataaag cccctggtg ttttaccaca     1320 gaccccagcg tcaggtggga gtactgcaac ctgaaaaaat gctcaggaac agaagcgagt    1380
```

```
gttgtagcac ctccgcctgt tgtcctgctt ccagatgtag agactccttc cgaagaagac    1440
tgtatgtttg ggaatgggaa aggataccga ggcaagaggg cgaccactgt tactgggacg    1500
ccatgccagg actgggctgc ccaggagccc catagacaca gcattttcac tccagagaca    1560
aatccacggg cgggtctgga aaaaaattac tgccgtaacc ctgatggtga tgtaggtggt    1620
ccctggtgct acacgacaaa tccaagaaaa ctttacgact actgtgatgt ccctcagtgt    1680
gcggccccct catttgattg tgggaagcct caagtggagc cgaagaaatg tcctggaagg    1740
gttgtagggg ggtgtgtggc ccacccacat tcctggccct ggcaagtcag tcttagaaca    1800
aggtttggaa tgcacttctg tggaggcacc ttgatatccc cagagtgggt gttgactgct    1860
gcccactgct tggagaagtc cccaaggcct tcatcctaca aggtcatcct gggtgcacac    1920
caagaagtga atctcgaacc gcatgttcag gaaatagaag tgtctaggct gttcttggag    1980
cccacacgaa aagatattgc cttgctaaag ctaagcagtc ctgccgtcat cactgacaaa    2040
gtaatcccag cttgtctgcc atccccaaat tatgtggtcg ctgaccggac cgaatgtttc    2100
atcactggct ggggagaaac ccaaggtact tttggagctg gccttctcaa ggaagcccag    2160
ctccctgtga ttgagaataa agtgtgcaat cgctatgagt ttctgaatgg aagagtccaa    2220
tccaccgaac tctgtgctgg gcatttggcc ggaggcactg acagttgcca gggtgacagt    2280
ggaggtcctc tggtttgctt cgagaaggac aaatacattt tacaaggagt cacttcttgg    2340
ggtcttggct gtgcacgccc caataagcct ggtgtctatg ttcgtgtttc aaggtttgtt    2400
acttggattg agggagtgat gagaaataat taa                                 2433
```

<210> SEQ ID NO 4
<211> LENGTH: 810
<212> TYPE: PRT
<213> ORGANISM: Artificial sequence
<220> FEATURE:
<223> OTHER INFORMATION: amino acid sequence coding for the natural
      plasminogen (from swiss prot)with the signal peptide

<400> SEQUENCE: 4

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
                20                  25                  30

Leu Phe Ser Val Thr Lys Lys Gln Leu Gly Ala Gly Ser Ile Glu Glu
            35                  40                  45

Cys Ala Ala Lys Cys Glu Glu Asp Glu Glu Phe Thr Cys Arg Ala Phe
        50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys

```
              165                 170                 175
Asp Ile Leu Glu Cys Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Ser Ser Gly Pro Thr
            260                 265                 270

Tyr Gln Cys Leu Lys Gly Thr Gly Glu Asn Tyr Arg Gly Asn Val Ala
        275                 280                 285

Val Thr Val Ser Gly His Thr Cys Gln His Trp Ser Ala Gln Thr Pro
    290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335

Thr Thr Asn Ser Gln Val Arg Trp Glu Tyr Cys Lys Ile Pro Ser Cys
            340                 345                 350

Asp Ser Ser Pro Val Ser Thr Glu Gln Leu Ala Pro Thr Ala Pro Pro
        355                 360                 365

Glu Leu Thr Pro Val Val Gln Asp Cys Tyr His Gly Asp Gly Gln Ser
370                 375                 380

Tyr Arg Gly Thr Ser Ser Thr Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
        435                 440                 445

Cys Asn Leu Lys Lys Cys Ser Gly Thr Glu Ala Ser Val Val Ala Pro
    450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
    530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
            580                 585                 590
```

Pro Trp Gln Val Ser Leu Arg Thr Arg Phe Gly Met His Phe Cys Gly
            595                 600                 605

Gly Thr Leu Ile Ser Pro Glu Trp Val Leu Thr Ala Ala His Cys Leu
        610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
            660                 665                 670

Ser Pro Ala Val Ile Thr Asp Lys Val Ile Pro Ala Cys Leu Pro Ser
        675                 680                 685

Pro Asn Tyr Val Val Ala Asp Arg Thr Glu Cys Phe Ile Thr Gly Trp
690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 5
<211> LENGTH: 2145
<212> TYPE: DNA
<213> ORGANISM: Artificial sequence
<220> FEATURE:
<223> OTHER INFORMATION: nucleotide sequence coding for LYS77-PLG(Lys-
      plasminogen)

<400> SEQUENCE: 5
aaagtgtatc tctcagagtg caagactggg aatggaaaga actacagagg gacgatgtcc     60
aaaacaaaaa atggcatcac ctgtcaaaaa tggagttcca cttctcccca cagacctaga   120
ttctcacctg ctacacaccc ctcagaggga ctggaggaga actactgcag gaatccagac   180
aacgatccgc aggggccctg tgctatact actgatccag aaaagagata tgactactgc   240
gacattcttg agtgtgaaga ggaatgtatg cattgcagtg agaaaactta tgacggcaaa   300
atttccaaga ccatgtctgg actgaatgc caggcctggg actctcagag cccacacgct   360
catggataca ttccttccaa atttccaaac aagaacctga agaagaatta ctgtcgtaac   420
cccgataggg agctgcggcc ttggtgtttc accaccgacc caacaagcg ctgggaactt   480 tgtgacatcc cccgctgcac aacacctcca ccatcttctg gtcccaccta ccagtgtctg   540
aagggaacag gtgaaaacta tcgcgggaat gtggctgtta ccgtgtccgg gcacacctgt   600
cagcactgga gtgcacagac ccctcacaca cataacagga caccagaaaa cttcccctgc   660
aaaaatttgg atgaaaacta ctgccgcaat cctgacggaa aagggccccc atggtgccat   720
acaaccaaca gccaagtgcg gtgggagtac tgtaagatac cgtcctgtga ctcctcccca   780

```
gtatccacgg aacaattggc tcccacagca ccacctgagc taaccctgt ggtccaggac    840 tgctaccatg gtgatggaca gagctaccga ggcacatcct ccaccaccac cacaggaaag    900
aagtgtcagt cttggtcatc tatgacacca caccggcacc agaagacccc agaaaactac    960
ccaaatgctg gcctgacaat gaactactgc aggaatccag atgccgataa aggcccctgg   1020
tgttttacca cagaccccag cgtcaggtgg gagtactgca acctgaaaaa atgctcagga   1080
acagaagcga gtgttgtagc acctccgcct gttgtcctgc ttccagatgt agagactcct   1140
tccgaagaag actgtatgtt tgggaatggg aaaggatacc gaggcaagag ggcgaccact   1200
gttactggga cgccatgcca ggactgggct gcccaggagc ccatagaca cagcattttc   1260 actccagaga caaatccacg ggcgggtctg aaaaaaatt actgccgtaa ccctgatggt   1320
gatgtaggtg gtccctggtg ctacacgaca aatccaagaa aactttacga ctactgtgat   1380
gtccctcagt gtgcggcccc ttcatttgat tgtgggaagc tcaagtgga gccgaagaaa   1440 tgtcctggaa gggttgtagg ggggtgtgtg gcccacccac attcctggcc ctggcaagtc   1500
agtcttagaa caaggtttgg aatgcacttc tgtggaggca ccttgatatc cccagagtgg   1560
gtgttgactg ctgcccactg cttggagaag tccccaaggc cttcatccta caaggtcatc   1620
ctgggtgcac accaagaagt gaatctcgaa ccgcatgttc aggaaataga agtgtctagg   1680
ctgttcttgg agcccacacg aaaagatatt gccttgctaa agctaagcag tcctgccgtc   1740
atcactgaca aagtaatccc agcttgtctg ccatccccaa attatgtggt cgctgaccgg   1800
accgaatgtt tcatcactgg ctgggggaaa acccaaggta cttttggagc tggccttctc   1860
aaggaagccc agctccctgt gattgagaat aaagtgtgca atcgctatga gtttctgaat   1920
ggaagagtcc aatccaccga actctgtgct gggcatttgg ccggaggcac tgacagttgc   1980
cagggtgaca gtggaggtcc tctggttgc ttcgagaagg acaaatacat tttacaagga   2040
gtcacttctt ggggtcttgg ctgtgcacgc cccaataagc ctggtgtcta tgttcgtgtt   2100
tcaaggtttg ttacttggat tgagggagtg atgagaaata attaa                  2145
```

<210> SEQ ID NO 6
<211> LENGTH: 714
<212> TYPE: PRT
<213> ORGANISM: Artificial sequence
<220> FEATURE:
<223> OTHER INFORMATION: amino acid sequence of LYS77-PLG(Lys-plasminogen)

<400> SEQUENCE: 6

Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

```
Trp Asp Ser Gln Ser Pro His Ala His Gly Tyr Ile Pro Ser Lys Phe
            115                 120                 125
Pro Asn Lys Asn Leu Lys Lys Asn Tyr Cys Arg Asn Pro Asp Arg Glu
        130                 135                 140
Leu Arg Pro Trp Cys Phe Thr Thr Asp Pro Asn Lys Arg Trp Glu Leu
145                 150                 155                 160
Cys Asp Ile Pro Arg Cys Thr Thr Pro Pro Ser Ser Gly Pro Thr
                165                 170                 175
Tyr Gln Cys Leu Lys Gly Thr Gly Glu Asn Tyr Arg Gly Asn Val Ala
            180                 185                 190
Val Thr Val Ser Gly His Thr Cys Gln His Trp Ser Ala Gln Thr Pro
        195                 200                 205
His Thr His Asn Arg Thr Pro Glu Asn Phe Pro Cys Lys Asn Leu Asp
        210                 215                 220
Glu Asn Tyr Cys Arg Asn Pro Asp Gly Lys Arg Ala Pro Trp Cys His
225                 230                 235                 240
Thr Thr Asn Ser Gln Val Arg Trp Glu Tyr Cys Lys Ile Pro Ser Cys
                245                 250                 255
Asp Ser Ser Pro Val Ser Thr Glu Gln Leu Ala Pro Thr Ala Pro Pro
            260                 265                 270
Glu Leu Thr Pro Val Val Gln Asp Cys Tyr His Gly Asp Gly Gln Ser
        275                 280                 285
Tyr Arg Gly Thr Ser Ser Thr Thr Thr Gly Lys Lys Cys Gln Ser
        290                 295                 300
Trp Ser Ser Met Thr Pro His Arg His Gln Lys Thr Pro Glu Asn Tyr
305                 310                 315                 320
Pro Asn Ala Gly Leu Thr Met Asn Tyr Cys Arg Asn Pro Asp Ala Asp
                325                 330                 335
Lys Gly Pro Trp Cys Phe Thr Thr Asp Pro Ser Val Arg Trp Glu Tyr
            340                 345                 350
Cys Asn Leu Lys Lys Cys Ser Gly Thr Glu Ala Ser Val Val Ala Pro
        355                 360                 365
Pro Pro Val Val Leu Leu Pro Asp Val Glu Thr Pro Ser Glu Glu Asp
370                 375                 380
Cys Met Phe Gly Asn Gly Lys Gly Tyr Arg Gly Lys Arg Ala Thr Thr
385                 390                 395                 400
Val Thr Gly Thr Pro Cys Gln Asp Trp Ala Ala Gln Glu Pro His Arg
                405                 410                 415
His Ser Ile Phe Thr Pro Glu Thr Asn Pro Arg Ala Gly Leu Glu Lys
                420                 425                 430
Asn Tyr Cys Arg Asn Pro Asp Gly Asp Val Gly Gly Pro Trp Cys Tyr
        435                 440                 445
Thr Thr Asn Pro Arg Lys Leu Tyr Asp Tyr Cys Asp Val Pro Gln Cys
        450                 455                 460
Ala Ala Pro Ser Phe Asp Cys Gly Lys Pro Gln Val Glu Pro Lys Lys
465                 470                 475                 480
Cys Pro Gly Arg Val Val Gly Gly Cys Val Ala His Pro His Ser Trp
                485                 490                 495
Pro Trp Gln Val Ser Leu Arg Thr Arg Phe Gly Met His Phe Cys Gly
            500                 505                 510
Gly Thr Leu Ile Ser Pro Glu Trp Val Leu Thr Ala Ala His Cys Leu
        515                 520                 525
Glu Lys Ser Pro Arg Pro Ser Ser Tyr Lys Val Ile Leu Gly Ala His
```

```
            530             535             540
Gln Glu Val Asn Leu Glu Pro His Val Gln Glu Ile Glu Val Ser Arg
545                 550                 555                 560

Leu Phe Leu Glu Pro Thr Arg Lys Asp Ile Ala Leu Leu Lys Leu Ser
                565                 570                 575

Ser Pro Ala Val Ile Thr Asp Lys Val Ile Pro Ala Cys Leu Pro Ser
            580                 585                 590

Pro Asn Tyr Val Val Ala Asp Arg Thr Glu Cys Phe Ile Thr Gly Trp
        595                 600                 605

Gly Glu Thr Gln Gly Thr Phe Gly Ala Gly Leu Leu Lys Glu Ala Gln
    610                 615                 620

Leu Pro Val Ile Glu Asn Lys Val Cys Asn Arg Tyr Glu Phe Leu Asn
625                 630                 635                 640

Gly Arg Val Gln Ser Thr Glu Leu Cys Ala Gly His Leu Ala Gly Gly
                645                 650                 655

Thr Asp Ser Cys Gln Gly Asp Ser Gly Gly Pro Leu Val Cys Phe Glu
            660                 665                 670

Lys Asp Lys Tyr Ile Leu Gln Gly Val Thr Ser Trp Gly Leu Gly Cys
        675                 680                 685

Ala Arg Pro Asn Lys Pro Gly Val Tyr Val Arg Val Ser Arg Phe Val
    690                 695                 700

Thr Trp Ile Glu Gly Val Met Arg Asn Asn
705                 710

<210> SEQ ID NO 7
<211> LENGTH: 1245
<212> TYPE: DNA
<213> ORGANISM: Artificial sequence
<220> FEATURE:
<223> OTHER INFORMATION: nucleotide sequence coding for delta-plg(delta-
      plasminogen)

<400> SEQUENCE: 7
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt atttgaaaaa gaaagtgtat     240
ctctcagagt gcaagactgg gaatggaaag aactacagag gacgatgtc caaaacaaaa     300 aatggcatca cctgtcaaaa atggagttcc acttctcccc acagacctag attctcacct     360
gctacacacc cctcagaggg actggaggag aactactgca ggaatccaga caacgatccg     420
caggggccct ggtgctatac tactgatcca gaaaagagat atgactactg cgacattctt     480
gagtgtgaag aggcggcccc ttcatttgat tgtgggaagc tcaagtgga gccgaagaaa     540 tgtcctggaa gggttgtagg ggggtgtgtg gcccacccac attcctggcc ctggcaagtc     600
agtcttagaa caaggtttgg aatgcacttc tgtggaggca ccttgatatc cccagagtgg     660
gtgttgactg ctgcccactg cttggagaag tccccaaggc cttcatccta caaggtcatc     720
ctgggtgcac accaagaagt gaatctcgaa ccgcatgttc aggaaatag agtgtctagg     780 ctgttcttgg agcccacacg aaaagatatt gccttgctaa agctaagcag tcctgccgtc     840
atcactgaca agtaatccc agcttgtctg ccatccccaa attatgtggt cgctgaccgg     900
accgaatgtt tcatcactgg ctggggagaa acccaaggta cttttggagc tggccttctc     960
aaggaagccc agctccctgt gattgagaat aaagtgtgca atcgctatga gtttctgaat    1020
```

```
ggaagagtcc aatccaccga actctgtgct gggcatttgg ccggaggcac tgacagttgc   1080
cagggtgaca gtggaggtcc tctggtttgc ttcgagaagg acaaatacat tttacaagga   1140
gtcacttctt ggggtcttgg ctgtgcacgc cccaataagc ctggtgtcta tgttcgtgtt   1200
tcaaggtttg ttacttggat tgagggagtg atgagaaata attaa                  1245
```

<210> SEQ ID NO 8
<211> LENGTH: 414
<212> TYPE: PRT
<213> ORGANISM: Artificial sequence
<220> FEATURE:
<223> OTHER INFORMATION: amino acid sequence of delta-plg(delta-plasminogen)

<400> SEQUENCE: 8

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Ala Ala Pro Ser Phe Asp Cys Gly Lys Pro Gln Val
                165                 170                 175

Glu Pro Lys Lys Cys Pro Gly Arg Val Val Gly Gly Cys Val Ala His
            180                 185                 190

Pro His Ser Trp Pro Trp Gln Val Ser Leu Arg Thr Arg Phe Gly Met
        195                 200                 205

His Phe Cys Gly Gly Thr Leu Ile Ser Pro Glu Trp Val Leu Thr Ala
    210                 215                 220

Ala His Cys Leu Glu Lys Ser Pro Arg Pro Ser Ser Tyr Lys Val Ile
225                 230                 235                 240

Leu Gly Ala His Gln Glu Val Asn Leu Glu Pro His Val Gln Glu Ile
                245                 250                 255

Glu Val Ser Arg Leu Phe Leu Glu Pro Thr Arg Lys Asp Ile Ala Leu
            260                 265                 270

Leu Lys Leu Ser Ser Pro Ala Val Ile Thr Asp Lys Val Ile Pro Ala
        275                 280                 285

Cys Leu Pro Ser Pro Asn Tyr Val Val Ala Asp Arg Thr Glu Cys Phe
    290                 295                 300

Ile Thr Gly Trp Gly Glu Thr Gln Gly Thr Phe Gly Ala Gly Leu Leu
305                 310                 315                 320
```

Lys Glu Ala Gln Leu Pro Val Ile Glu Asn Lys Val Cys Asn Arg Tyr
                325                 330                 335

Glu Phe Leu Asn Gly Arg Val Gln Ser Thr Glu Leu Cys Ala Gly His
            340                 345                 350

Leu Ala Gly Gly Thr Asp Ser Cys Gln Gly Asp Ser Gly Gly Pro Leu
        355                 360                 365

Val Cys Phe Glu Lys Asp Lys Tyr Ile Leu Gln Gly Val Thr Ser Trp
370                 375                 380

Gly Leu Gly Cys Ala Arg Pro Asn Lys Pro Gly Val Tyr Val Arg Val
385                 390                 395                 400

Ser Arg Phe Val Thr Trp Ile Glu Gly Val Met Arg Asn Asn
                405                 410

<210> SEQ ID NO 9
<211> LENGTH: 1104
<212> TYPE: DNA
<213> ORGANISM: Artificial sequence
<220> FEATURE:
<223> OTHER INFORMATION: nucleotide sequence coding for Mini-plg(mini-
      plasminogen)

<400> SEQUENCE: 9
gtcaggtggg agtactgcaa cctgaaaaaa tgctcaggaa cagaagcgag tgttgtagca        60
cctccgcctg ttgtcctgct tccagatgta gagactcctt ccgaagaaga ctgtatgttt       120
gggaatggga aggataccg aggcaagagg gcgaccactg ttactgggac gccatgccag        180
gactgggctg cccaggagcc ccatagacac agcattttca ctccagagac aaatccacgg       240
gcgggtctgg aaaaaaatta ctgccgtaac cctgatggtg atgtaggtgg ccctggtgc        300 tacacgacaa atccaagaaa actttacgac tactgtgatg tccctcagtg tgcggcccct       360
tcatttgatt gtgggaagcc tcaagtggag ccgaagaaat gtcctggaag ggttgtaggg       420
gggtgtgtgg cccacccaca ttcctggccc tggcaagtca gtcttagaac aaggtttgga       480
atgcacttct gtggaggcac cttgatatcc cagagtgggt gttgactgc tgcccactgc        540 ttggagaagt ccccaaggcc ttcatcctac aaggtcatcc tgggtgcaca ccaagaagtg       600
aatctcgaac cgcatgttca ggaaatagaa gtgtctaggc tgttcttgga gcccacacga       660
aaagatattg ccttgctaaa gctaagcagt cctgccgtca tcactgacaa agtaatccca       720
gcttgtctgc catccccaaa ttatgtggtc gctgaccgga ccgaatgttt catcactggc       780
tggggagaaa cccaaggtac ttttggagct ggccttctca aggaagccca gctccctgtg       840
attgagaata agtgtgcaa tcgctatgag tttctgaatg gaagagtcca atccaccgaa       900
ctctgtgctg gcatttggc cggaggcact gacagttgcc agggtgacag tggaggtcct       960
ctggtttgct tcgagaagga caaatacatt ttacaaggag tcacttcttg gggtcttggc      1020
tgtgcacgcc caataagcc tggtgtctat gttcgtgttt caaggtttgt tacttggatt      1080
gagggagtga tgagaaataa ttaa                                             1104

<210> SEQ ID NO 10
<211> LENGTH: 367
<212> TYPE: PRT
<213> ORGANISM: Artificial sequence
<220> FEATURE:
<223> OTHER INFORMATION: amino acid sequence of Mini-plg(mini-
      plasminogen)

<400> SEQUENCE: 10

Val Arg Trp Glu Tyr Cys Asn Leu Lys Lys Cys Ser Gly Thr Glu Ala
1               5                   10                  15

Ser Val Val Ala Pro Pro Val Leu Leu Pro Asp Val Glu Thr
            20              25              30

Pro Ser Glu Glu Asp Cys Met Phe Gly Asn Gly Lys Gly Tyr Arg Gly
        35              40              45

Lys Arg Ala Thr Thr Val Thr Gly Thr Pro Cys Gln Asp Trp Ala Ala
    50              55              60

Gln Glu Pro His Arg His Ser Ile Phe Thr Pro Glu Thr Asn Pro Arg
65              70              75              80

Ala Gly Leu Glu Lys Asn Tyr Cys Arg Asn Pro Asp Gly Asp Val Gly
            85              90              95

Gly Pro Trp Cys Tyr Thr Thr Asn Pro Arg Lys Leu Tyr Asp Tyr Cys
        100             105             110

Asp Val Pro Gln Cys Ala Ala Pro Ser Phe Asp Cys Gly Lys Pro Gln
        115             120             125

Val Glu Pro Lys Lys Cys Pro Gly Arg Val Val Gly Gly Cys Val Ala
    130             135             140

His Pro His Ser Trp Pro Trp Gln Val Ser Leu Arg Thr Arg Phe Gly
145             150             155             160

Met His Phe Cys Gly Gly Thr Leu Ile Ser Pro Glu Trp Val Leu Thr
            165             170             175

Ala Ala His Cys Leu Glu Lys Ser Pro Arg Pro Ser Ser Tyr Lys Val
        180             185             190

Ile Leu Gly Ala His Gln Glu Val Asn Leu Glu Pro His Val Gln Glu
    195             200             205

Ile Glu Val Ser Arg Leu Phe Leu Glu Pro Thr Arg Lys Asp Ile Ala
    210             215             220

Leu Leu Lys Leu Ser Ser Pro Ala Val Ile Thr Asp Lys Val Ile Pro
225             230             235             240

Ala Cys Leu Pro Ser Pro Asn Tyr Val Val Ala Asp Arg Thr Glu Cys
            245             250             255

Phe Ile Thr Gly Trp Gly Glu Thr Gln Gly Thr Phe Gly Ala Gly Leu
        260             265             270

Leu Lys Glu Ala Gln Leu Pro Val Ile Glu Asn Lys Val Cys Asn Arg
    275             280             285

Tyr Glu Phe Leu Asn Gly Arg Val Gln Ser Thr Glu Leu Cys Ala Gly
    290             295             300

His Leu Ala Gly Gly Thr Asp Ser Cys Gln Gly Asp Ser Gly Gly Pro
305             310             315             320

Leu Val Cys Phe Glu Lys Asp Lys Tyr Ile Leu Gln Gly Val Thr Ser
            325             330             335

Trp Gly Leu Gly Cys Ala Arg Pro Asn Lys Pro Gly Val Tyr Val Arg
        340             345             350

Val Ser Arg Phe Val Thr Trp Ile Glu Gly Val Met Arg Asn Asn
    355             360             365

<210> SEQ ID NO 11
<211> LENGTH: 750
<212> TYPE: DNA
<213> ORGANISM: Artificial sequence
<220> FEATURE:
<223> OTHER INFORMATION: nucleotide sequence coding for Micro-plg(micro-
      plasminogen)

<400> SEQUENCE: 11

```
gccccttcat tgattgtgg gaagcctcaa gtggagccga agaaatgtcc tggaagggtt        60 gtagggggt gtgtggccca cccacattcc tggccctggc aagtcagtct tagaacaagg       120
tttggaatgc acttctgtgg aggcaccttg atatccccag agtgggtgtt gactgctgcc      180
cactgcttgg agaagtcccc aaggccttca tcctacaagg tcatcctggg tgcacaccaa      240
gaagtgaatc tcgaaccgca tgttcaggaa atagaagtgt ctaggctgtt cttggagccc      300
acacgaaaag atattgcctt gctaaagcta agcagtcctg ccgtcatcac tgacaaagta      360
atcccagctt gtctgccatc cccaaattat gtggtcgctg accggaccga atgtttcatc      420
actggctggg gagaaaccca aggtactttt ggagctggcc ttctcaagga agcccagctc      480
cctgtgattg agaataaagt gtgcaatcgc tatgagtttc tgaatggaag agtccaatcc      540
accgaactct gtgctgggca tttggccgga ggcactgaca gttgccaggg tgacagtgga      600
ggtcctctgg tttgcttcga aaaggacaaa tacattttac aaggagtcac ttcttggggt      660
cttggctgtg cacgccccaa taagcctggt gtctatgttc gtgtttcaag gtttgttact      720
tggattgagg gagtgatgag aaataattaa                                        750

<210> SEQ ID NO 12
<211> LENGTH: 249
<212> TYPE: PRT
<213> ORGANISM: Artificial sequence
<220> FEATURE:
<223> OTHER INFORMATION: amino acid sequence coding for Micro-plg(micro-
      plasminogen)

<400> SEQUENCE: 12

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220
```

Arg Pro Asn Lys Pro Gly Val Tyr Val Arg Val Ser Arg Phe Val Thr
225                 230                 235                 240

Trp Ile Glu Gly Val Met Arg Asn Asn
                245

<210> SEQ ID NO 13
<211> LENGTH: 684
<212> TYPE: DNA
<213> ORGANISM: Artificial sequence
<220> FEATURE:
<223> OTHER INFORMATION: nucleotide sequence coding for the serine
      protease domain

<400> SEQUENCE: 13

```
gttgtagggg ggtgtgtggc ccacccacat tcctggccct ggcaagtcag tcttagaaca      60
aggtttggaa tgcacttctg tggaggcacc ttgatatccc cagagtgggt gttgactgct     120
gcccactgct tggagaagtc cccaaggcct tcatcctaca aggtcatcct gggtgcacac     180
caagaagtga atctcgaacc gcatgttcag gaaatagaag tgtctaggct gttcttggag     240
cccacacgaa aagatattgc cttgctaaag ctaagcagtc ctgccgtcat cactgacaaa     300
gtaatcccag cttgtctgcc atccccaaat tatgtggtcg ctgaccggac cgaatgtttc     360
atcactggct ggggagaaac ccaaggtact tttggagctg gccttctcaa ggaagcccag     420
ctccctgtga ttgagaataa agtgtgcaat cgctatgagt ttctgaatgg aagagtccaa     480
tccaccgaac tctgtgctgg gcatttggcc ggaggcactg acagttgcca gggtgacagt     540
ggaggtcctc tggtttgctt cgagaaggac aaatacattt tacaaggagt cacttcttgg     600
ggtcttggct gtgcacgccc caataagcct ggtgtctatg ttcgtgtttc aaggtttgtt     660
acttggattg agggagtgat gaga                                           684
```

<210> SEQ ID NO 14
<211> LENGTH: 228
<212> TYPE: PRT
<213> ORGANISM: Artificial sequence
<220> FEATURE:
<223> OTHER INFORMATION: amino acid sequence coding for the serine
      protease domain

<400> SEQUENCE: 14

Val Val Gly Gly Cys Val Ala His Pro His Ser Trp Pro Trp Gln Val
1               5                   10                  15

Ser Leu Arg Thr Arg Phe Gly Met His Phe Cys Gly Gly Thr Leu Ile
            20                  25                  30

Ser Pro Glu Trp Val Leu Thr Ala Ala His Cys Leu Glu Lys Ser Pro
        35                  40                  45

Arg Pro Ser Ser Tyr Lys Val Ile Leu Gly Ala His Gln Glu Val Asn
    50                  55                  60

Leu Glu Pro His Val Gln Glu Ile Glu Val Ser Arg Leu Phe Leu Glu
65                  70                  75                  80

Pro Thr Arg Lys Asp Ile Ala Leu Leu Lys Leu Ser Ser Pro Ala Val
                85                  90                  95

Ile Thr Asp Lys Val Ile Pro Ala Cys Leu Pro Ser Pro Asn Tyr Val
            100                 105                 110

Val Ala Asp Arg Thr Glu Cys Phe Ile Thr Gly Trp Gly Glu Thr Gln
        115                 120                 125

Gly Thr Phe Gly Ala Gly Leu Leu Lys Glu Ala Gln Leu Pro Val Ile
    130                 135                 140

```
Glu Asn Lys Val Cys Asn Arg Tyr Glu Phe Leu Asn Gly Arg Val Gln
145                 150                 155                 160

Ser Thr Glu Leu Cys Ala Gly His Leu Ala Gly Gly Thr Asp Ser Cys
                165                 170                 175

Gln Gly Asp Ser Gly Gly Pro Leu Val Cys Phe Glu Lys Asp Lys Tyr
            180                 185                 190

Ile Leu Gln Gly Val Thr Ser Trp Gly Leu Gly Cys Ala Arg Pro Asn
        195                 200                 205

Lys Pro Gly Val Tyr Val Arg Val Ser Arg Phe Val Thr Trp Ile Glu
    210                 215                 220

Gly Val Met Arg
225
```